(12) United States Patent
Oshinowo

(10) Patent No.: US 10,238,992 B2
(45) Date of Patent: Mar. 26, 2019

(54) PROCESSES FOR ANALYSIS AND OPTIMIZATION OF MULTIPHASE SEPARATORS, PARTICULARLY IN REGARD TO SIMULATED GRAVITY SEPARATION OF IMMISCIBLE LIQUID DISPERSIONS

(71) Applicant: Saudi Arabian Oil Company, Dhahran (SA)

(72) Inventor: Olanrewaju Malcolm Oshinowo, Dhahran (SA)

(73) Assignee: SAUDI ARABIAN OIL COMPANY, Dhahran (SA)

(*) Notice: Subject to any disclaimer, the term of this patent is extended or adjusted under 35 U.S.C. 154(b) by 249 days.

(21) Appl. No.: 15/145,606

(22) Filed: May 3, 2016

(65) Prior Publication Data
US 2017/0319984 A1 Nov. 9, 2017

(51) Int. Cl.
*B01D 17/02* (2006.01)
*B01D 17/12* (2006.01)
(Continued)

(52) U.S. Cl.
CPC ......... *B01D 17/12* (2013.01); *B01D 17/0208* (2013.01); *B01D 21/30* (2013.01);
(Continued)

(58) Field of Classification Search
CPC ............... B01D 17/02; B01D 17/0208; B01D 17/0211; B01D 17/0214; B01D 17/04;
(Continued)

(56) References Cited

U.S. PATENT DOCUMENTS

| 4,226,714 A * | 10/1980 | Furness | B01D 21/01 210/723 |
| 4,273,658 A * | 6/1981 | Karman | B01D 21/01 210/709 |

(Continued)

FOREIGN PATENT DOCUMENTS

WO 2015110599 A1 7/2015

OTHER PUBLICATIONS

Publication by Trivikram Nallamilli et al, "A Model for the Prediction of Droplet Size in Pickering Emulsions Stabilized by Oppositely Charged Particles", Published in Langmuir, vol. 30, Jul. 23, 2014, pp. 9336-9345.*

(Continued)

*Primary Examiner* — Joseph W Drodge
(74) *Attorney, Agent, or Firm* — Leason Ellis LLP

(57) ABSTRACT

The present invention is directed to systems and methods for evaluating performance, performing process control, optimization and design of gravity separation process systems that are used to separate immiscible liquid dispersions (e.g., water-in-oil, oil-in-water mixtures) and emulsions for two-phase (liquid-liquid) or three-phase (gas-liquid-liquid) systems. According to one aspect, the design, simulation and control of such systems is performed using computational fluid dynamics (CFD) software that is configured for determining the separation efficiency of separators on the basis of the true geometry and multidimensional flow field and for a distribution of droplet sizes with the influence of the emulsion concentration on the rheology of the oil-in-water or water-in-oil dispersion. The results of the CFD simulations can be used to adjust input parameters of the separator to maximize the separation efficiency of the separator such that it outputs liquid streams containing minimal amounts of immiscible liquid dispersions.

20 Claims, 12 Drawing Sheets

(51) Int. Cl.
  *B01D 21/30* (2006.01)
  *B01D 21/34* (2006.01)
  *G05B 13/04* (2006.01)
  *G06F 17/13* (2006.01)
  *G06F 19/00* (2018.01)

(52) U.S. Cl.
  CPC .......... *B01D 21/34* (2013.01); *G05B 13/041* (2013.01); *G06F 17/13* (2013.01); *G06F 19/702* (2013.01)

(58) Field of Classification Search
  CPC ...... B01D 17/045; B01D 17/12; B01D 21/00; B01D 21/003; B01D 21/0039; B01D 21/30; B01D 21/302; B01D 21/32; B01D 21/34; G06F 17/13; G06F 19/702; G06F 7/48; G06F 7/50; G05B 13/04; G05B 13/041; G05B 13/042; G05B 13/048; G06G 7/57; G06G 7/58; G06G 7/66; G05D 11/131; G05D 11/135; G05D 11/136; G05D 11/137; G05D 11/138; G05D 11/139; G06N 5/00; G06N 5/02; G06N 5/022; G06N 5/025; G06N 7/00; G06N 99/00; G06Q 50/00
  USPC ... 210/739, 799–803, 85, 86, 143, 207, 513, 210/521, 522; 702/50, 55; 700/271, 273, 700/281, 282; 703/2, 6, 7, 9, 10; 706/919–923
  See application file for complete search history.

(56) References Cited

U.S. PATENT DOCUMENTS

| | | | | |
|---|---|---|---|---|
| 5,774,633 | A * | 6/1998 | Baba | G05B 13/027 210/143 |
| 7,698,110 | B2 * | 4/2010 | Connor | G06F 17/509 703/1 |
| 8,197,700 | B2 * | 6/2012 | Beyk | B01D 17/0214 210/800 |
| 2003/0217971 | A1 * | 11/2003 | Varadaraj | B01D 17/045 210/639 |
| 2005/0288912 | A1 * | 12/2005 | Asprion | G05B 17/02 703/9 |
| 2007/0267325 | A1 * | 11/2007 | Vu | C10G 31/06 208/187 |
| 2010/0106467 | A1 * | 4/2010 | Attarakih | G06F 17/5009 703/2 |
| 2012/0125868 | A1 * | 5/2012 | Falappi | B01D 17/0211 210/800 |
| 2012/0166158 | A1 * | 6/2012 | El Giheny | G01N 15/02 703/2 |
| 2013/0218538 | A1 * | 8/2013 | Fuecker | G06F 17/5018 703/2 |
| 2014/0207415 | A1 * | 7/2014 | Bhutani | G06Q 10/06 702/182 |
| 2014/0207430 | A1 * | 7/2014 | Li | E21B 41/00 703/2 |
| 2014/0343909 | A1 * | 11/2014 | Guerillot | G01V 11/00 703/2 |
| 2015/0286755 | A1 | 10/2015 | Johansen | |
| 2016/0053455 | A1 * | 2/2016 | Lundback | E02B 15/106 210/242.1 |

OTHER PUBLICATIONS

Publication by Christine Noik et al, "Modeling of Liquid/Liquid Phase Separation: Application to Petroleum Emulsions", Journal of Dispersion Science and Technology, vol. 34:8, Published Jul. 23, 2013, pp. 1029-1042.*
Hansen. "Phenomeological Modelling and Simulation of Fluid Flow and Separation Behaviour in Offshore Gravity Separators." PVP-vol. 431, Emerging Technologies for Fluids, Structures and Fluid-Structure Interaction—2001. ASME 2001. 7 pages.
Kharoua et al. "CFD Modelling of a Horizontal Three-Phase Separator: A Population Balance Approach." American Journal of Fluid Dynamics 2013, 3(4), pp. 101-118.
Mazzei, L. "Eulerian modelling and computational fluid dynamics simulation of mono and polydisperse fluidized suspensions." Thesis. Department of Chemical Engineering, University College London. Oct. 2008. 211 pages.
International Search Report and Written Opinion for International Patent Application No. PCT/2017/027016 dated Oct. 17, 2017. 15 pages.
Laleh et al. "Computational Fluid Dynamics-Based Study of an Oilfield Separator—Part I: A Realistic Simulation." Oil and Gas Facilities 1.06 (2012): 57-68.
Laleh et al. "Computational Fluid Dynamics-Based Study of an Oilfield Separator—Part II: An Optimum Design." Oil and Gas Facilities 2.01 (2013): 52-59.
Laleh et al. "Design and CFD studies of multiphase separators—a review." The Canadian Journal of Chemical Engineering 90.6 (2012): 1547-1561.
Nydal. "Dynamic models in multiphase flow." Energy & Fuels 26.7 (2012): 4117-4123.
Wang et al. "Population balance model for gas—liquid flows: Influence of bubble coalescence and breakup models." Industrial & engineering chemistry research 44.19 (2005): 7540-7549.

* cited by examiner

Figure 7. Separator CFD Model process chart.

Figure 8. Separator performance work-flow.

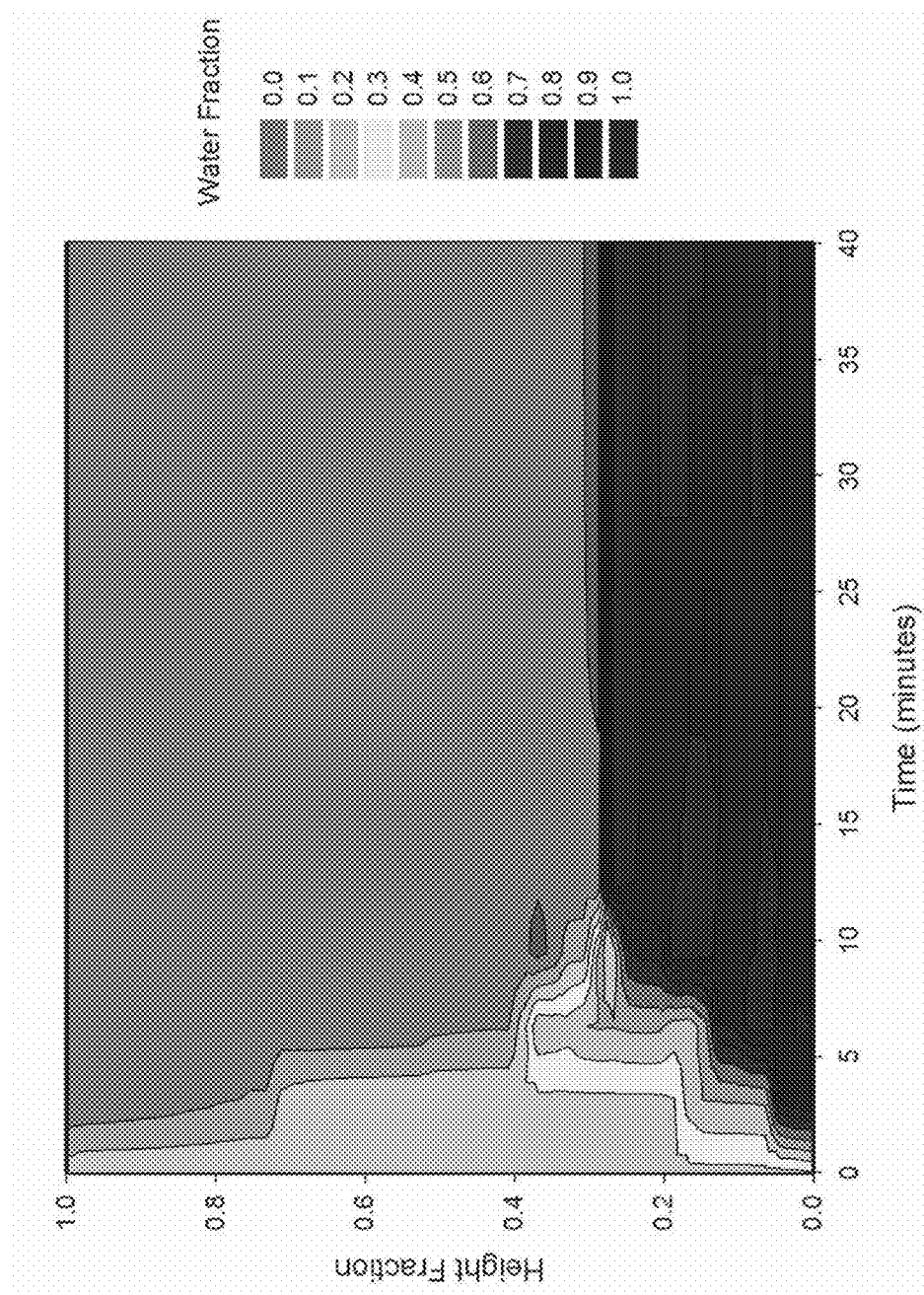
FIG. 9 (A). Added emulsion viscosity (modified Bullard model).

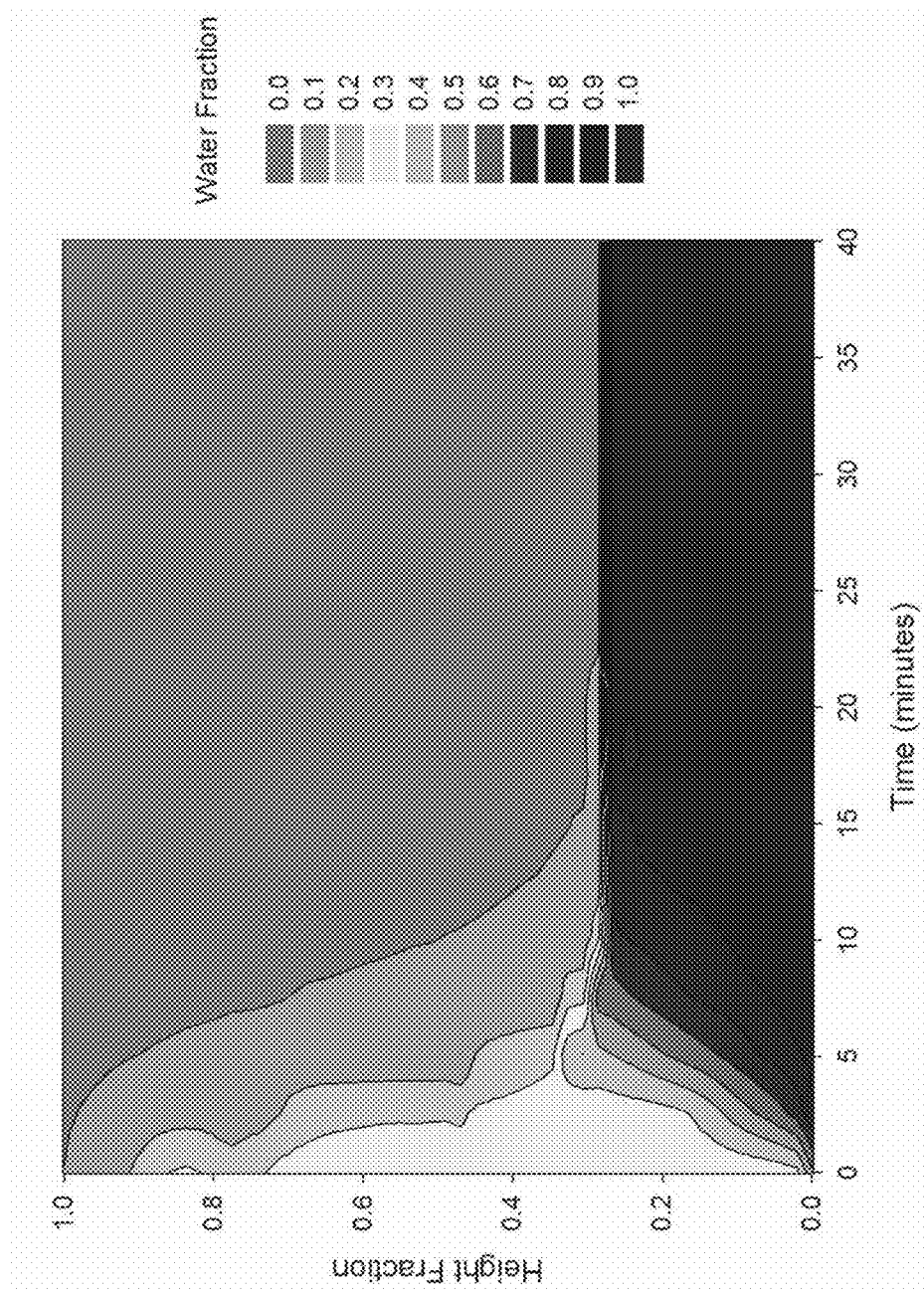
FIG. 9(B). Experimental measurement (Ultrasonic technique).

PROCESSES FOR ANALYSIS AND OPTIMIZATION OF MULTIPHASE SEPARATORS, PARTICULARLY IN REGARD TO SIMULATED GRAVITY SEPARATION OF IMMISCIBLE LIQUID DISPERSIONS

TECHNICAL FIELD OF THE INVENTION

The present invention relates to systems and processes for the separation of immiscible liquid dispersions. More specifically, the present invention relates to the design, monitoring, and/or and control of gravity separator process systems for gravity separation of water-in-oil or oil-in-water dispersions and emulsions.

BACKGROUND OF THE INVENTION

Crude oil and its fractions are used as feedstock for producing valuable chemicals. Crude oil in oil fields often times forms an emulsion with water.

An emulsion is a mixture of two or more liquids that are normally immiscible where one phase is discontinuously dispersed in the other ("continuous") phase. There are several types of oil/water emulsions including, water-in-oil (w/o) emulsions [water is the dispersed phase, oil is the continuous phase] and oil-in-water (o/w) emulsions [oil is the dispersed phase, water is the continuous phase], as well as more complex emulsions such as water-in-oil-in-water (w/o/w) emulsions and oil-in-water-in-oil (o/w/o) emulsions. More often than not, the emulsions produced in oil fields are w/o emulsions.

The separation of hydrocarbon gas and liquids and water is generally carried out in vertical or horizontal gravity separators where the two or three phases enter the separator and are separated into separate streams of hydrocarbon gas, hydrocarbon or lighter density liquid and water or heavier density liquid phase. The quality of the liquid streams exiting the separator is affected by the separator efficiency. With less than ideal efficiency or complete separation, some of the heavy liquid phase is carried out with the lighter liquid phase (water-in-oil) and some of the lighter phase is carried out with the heavy phase (oil-in-water). In the process of transportation from the production well to the separator, the fluids mix and are dispersed into one another forming a complex dispersion or emulsion during pipeline transportation from the reservoir that is difficult to separate. The gas phase forms bubbles in the liquids and the liquid phases, hydrocarbon phase (lighter liquid phase) and the water phase (heavier liquid phase) intermingle forming an emulsion or dispersion of droplets of one phase in another.

While most of the gas separates quite easily, the emulsions are typically "tight" or stable and difficult to separate. The gravity separators operate on the principle of providing adequate settling time to the immiscible phases in a relatively quiet horizontal or vertical flow. The emulsion enters the separator and based on the amount of time provided by the capacity of the separation vessel, the phases separate to varying degrees where oil can be found in the water outlet stream and water in the oil outlet stream. Oil droplets rise to the oil-water interface and water droplets settle to the interface. The emulsion layer formed between the phases retards separation. Dispersions of oil and water are complicated by the inhomogeneity of the oil and the impurities in the water. Demulsifiers are added to improve oil-water separation and bottle tests, batch gravity separation, are used qualitatively to assess demulsifier effectiveness to accelerate oil-water separation.

Existing systems and methods for the design and sizing and control of gravity separators use techniques that are based on the retention time of fluids in the separator. These classic design guidelines lead to oversized designs that are costly, or unresponsive to changes in emulsion stability, or undersized and lacking the requisite efficiency. For instance, the retention time design criteria do not take into consideration the inlet conditions, emulsion stability, droplet size distribution, internals, or the water interface level. By way of further example, the design of separators based on the transport of a single droplet or the average retention time of the phase to be separated, typically do not take into account the multidimensional flow field in the separator and is prone to over-sizing the separator volume.

What is needed is a system and method for designing and controlling multiphase separators that allows the determination of the separation efficiency on the basis of the true geometry and multidimensional flow field and for a distribution of droplet sizes with the influence of the emulsion concentration on the rheology of the oil-in-water or water-in-oil dispersion thereby enabling designers, engineers and operators of facilities with separators to determine the phase distribution in the separator, the actual residence or retention time, and to optimize the separator for the prevailing operating conditions.

SUMMARY OF THE INVENTION

The present invention is directed to a computer-implemented method to evaluate the performance of a gravity separator system for separating a multi-liquid and multi-phase immiscible liquid dispersion, for monitoring of such systems, and for controlling such systems.

In one aspect, the method comprises the steps of: providing, at a processor of a controller computing device that is configured by executing code in the form of one or more modules stored in a non-transitory storage medium, operational input parameters. The operational input parameters include fluid property data for the immiscible liquid dispersion including one or more of density, viscosity and surface tension, static or dynamic settling data for the immiscible liquid dispersion, and geometry of an internal volume of the separator including one or more internal geometric components therein. The method also includes the step of generating, with the processor, a computational fluid dynamics (CFD) model of the separator system. In particular, generating the CFD model includes the steps of: defining, with the processor based on the geometry, a three-dimensional geometric model of the internal volume of the separator and the internal components therein; defining, with the processor based on the three-dimensional model, a computational mesh for the internal volume of the separator; determining, with the processor, an initial droplet size distribution of the immiscible liquid dispersion; representing volumes for each of a continuous gas phase, a heavier liquid phase and a lighter liquid phase within the interior volume of the separator using a Eulerian multiphase model; representing, for a volume of a dispersed liquid phase, a droplet size distribution with population balance modeling, wherein the distribution is modeled by solving a population balance equation according to multivariate methods; applying, with the processor, coalescence and breakage kernels to model droplet size evolution in the population as a function of droplet size and the fluid property data; and modeling the phase interaction between each of the continuous liquid phases and the dispersed liquid phase, wherein the model of the phase interaction is a function of the dispersed phase fraction concentration between dilute, semi-dilute and concentrated regimes within the dispersed liquid phase volume and is a function of a dispersed phase droplet diameter distribution, a dispersion viscosity, and oil and water properties. In addition, the method also includes the step of adjusting, with the processor based on the CFD model, one or more of the operational input parameters to maximize a separation efficiency and to output from the separator one or more streams of processed liquids having a respective prescribed composition.

In another aspect, the method comprises the step of providing a multiphase separator having an inlet for receiving a multi-liquid and multi-phase immiscible liquid dispersion comprising a gas phase, an oil phase, and a water phase. In a further aspect, the method comprises passing the immiscible liquid dispersion into the separator, adjusting the operational parameters to maximize the liquid-liquid separation efficiency, and outputting from the separator one or more streams of processed liquids separated from the immiscible liquid dispersion and containing minimal amounts of the immiscible liquid dispersion.

BRIEF DESCRIPTION OF THE DRAWING FIGURES

FIGS. 1A-B show diagrams depicting exemplary three-phase gas-oil-water separators having a weir (1A) and a boot (1B) in accordance with one or more of the disclosed embodiments;

Figure 10:
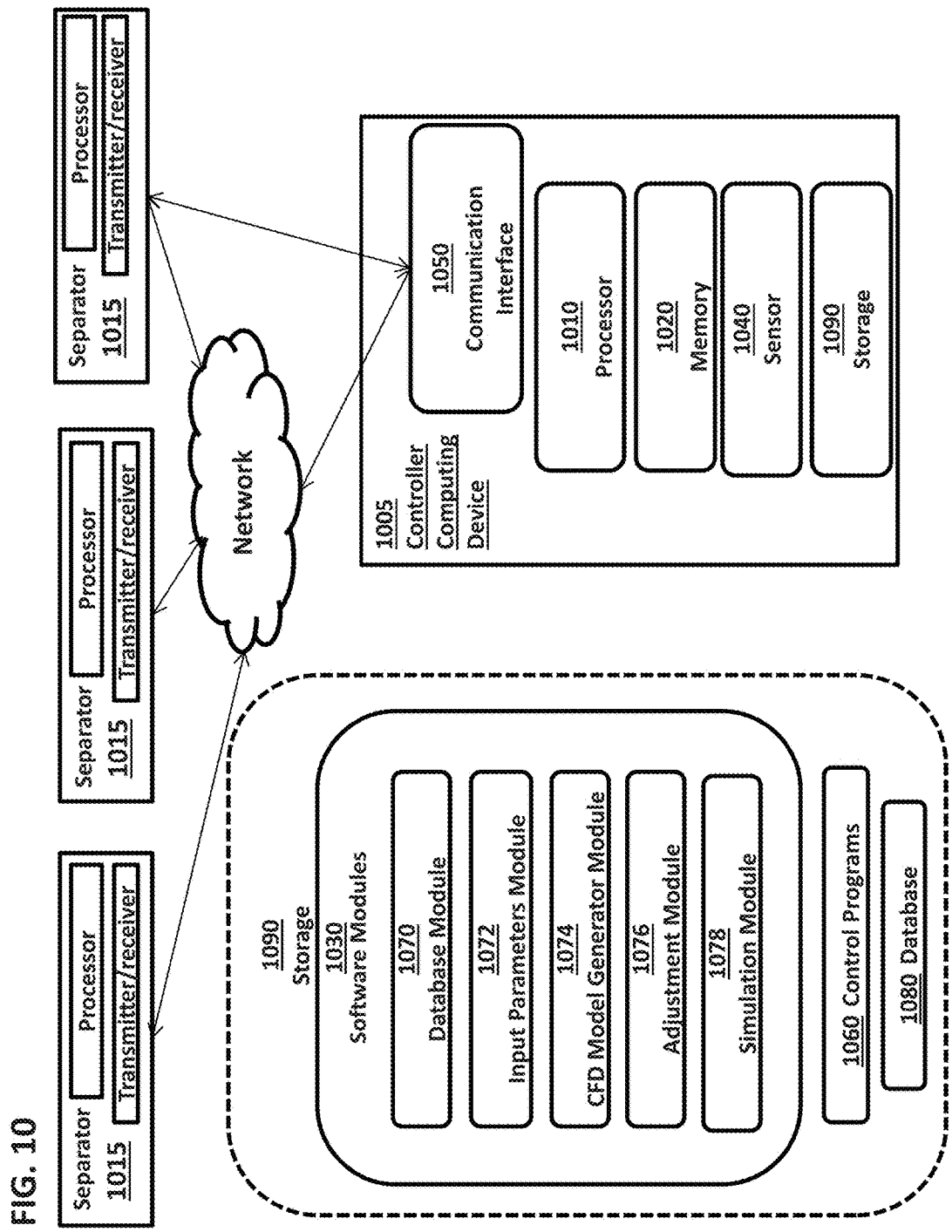

FIGS. 9A-B show graphs illustrating the height fraction over time for the water fractions using the modified Bullard model (9A) and the ultrasonic technique (9B) in accordance with one or more of the disclosed embodiments; and FIG. 10 is a high-level diagram illustrating an exemplary system for the separation of immiscible liquid dispersions, including hardware components suitable for implementing methods in accordance with one or more of the disclosed embodiments.

DETAILED DESCRIPTION OF CERTAIN EMBODIMENTS

The present invention is directed to systems and methods for evaluating performance, performing process control, optimization and design of gravity separation process systems that are used to separate immiscible liquid dispersions (e.g., water-in-oil, oil-in-water mixtures) and emulsions for two-phase (liquid-liquid) or three-phase (gas-liquid-liquid) systems.

According to one aspect, the design, simulation and control of such systems is performed using computational fluid dynamics (CFD) software that is configured for determining the separation efficiency of separators on the basis of the true geometry and multidimensional flow field and for a distribution of droplet sizes with the influence of the emulsion concentration on the rheology of the oil-in-water or water-in-oil dispersion. The present systems and methods utilize rigorous modeling with computational fluid dynamics to ensure proper capital expenditure and operational efficacy.

The exemplary systems and methods further described herein enable designers, engineers and operators of existing separators to determine the phase distribution in the separator and the actual residence or retention time, and to optimize the design of a new separator and operation of an existing separator based on the prevailing operating conditions. The systems and methods described herein can also be utilized as a training tool for engineers and operators to visualize virtual separator operations. Further, the present systems and methods can be used to evaluate and design novel separator internals in order to improve separation in horizontal, vertical, and two- or three-phase separators. Ultimately the systems and methods provide better predictions of separation efficiency to evaluate the operation of multiphase separators, to perform operational trouble-shooting, to perform process optimization, and to design new separator units.

A. Gravity Separation of Multi-Phase Oil and Water Dispersions

Figure 1A:
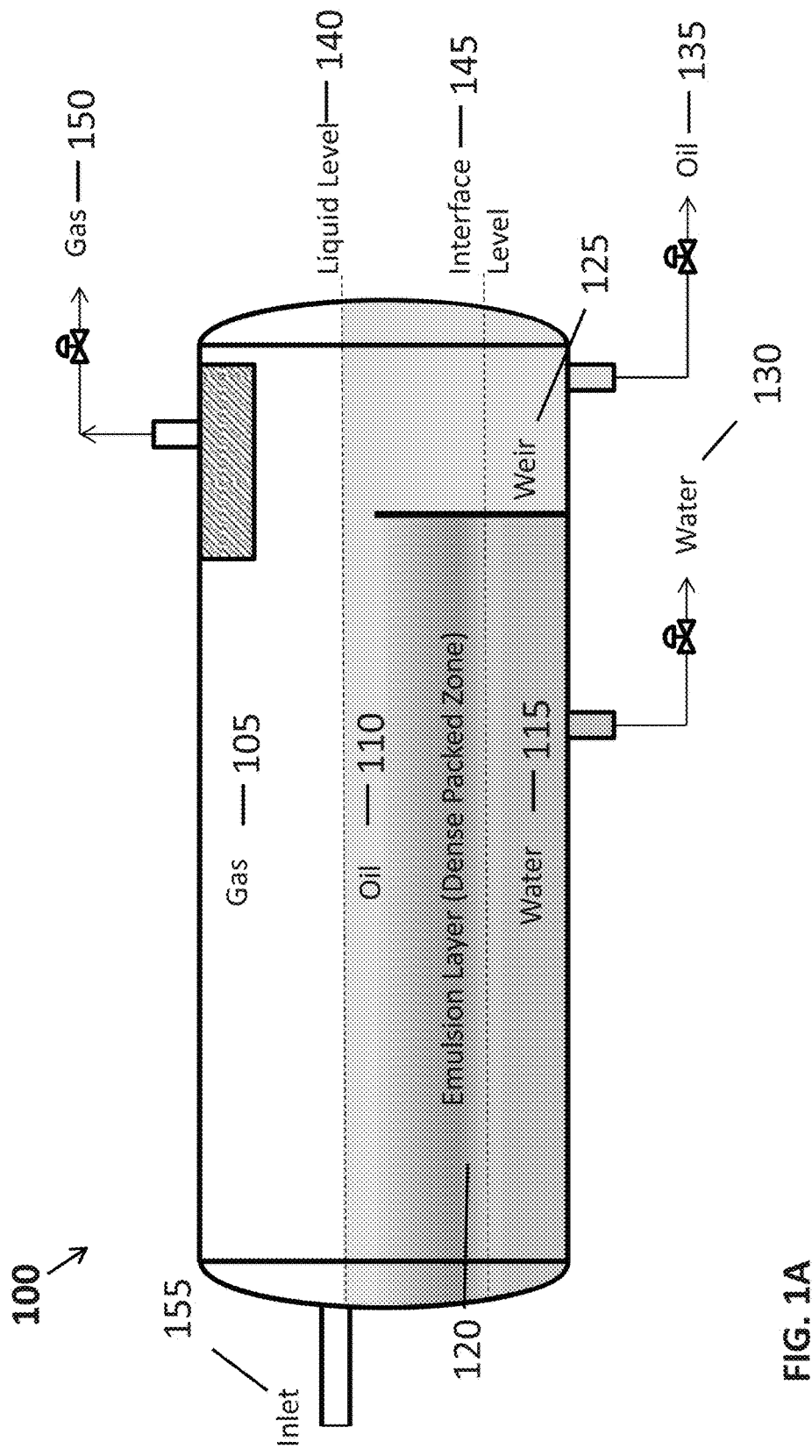
Figure 1B:
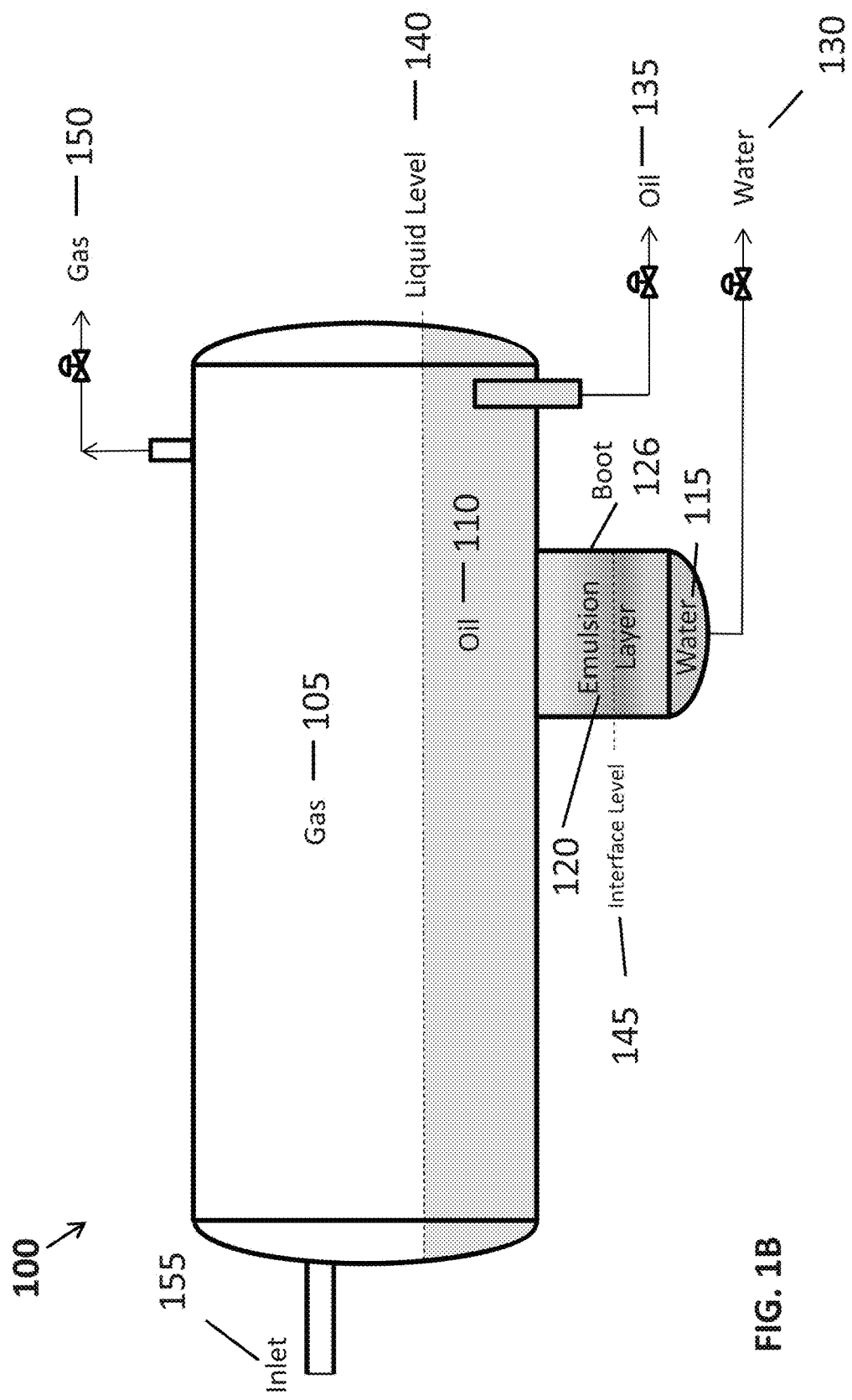

The co-existence of water and crude oil in the form of an emulsion is highly unattractive from both a process and product quality perspective. FIGS. 1A-B illustrate embodiments of a three phase separator 100 showing the exemplary phase separation regions therein including, Gas layer 105, Oil layer 110, Water layer 115 and an Emulsion Layer 120 between the Oil and Water layers. In the embodiment of FIG. 1A, also shown is a weir 125 for overflow of the lighter liquid phase (oil). FIG. 1B shows an alternative embodiment including a boot 126 designed for heavy phase removal. Control valves on the liquid phase outlets including, water outlet valve 130, oil outlet valve 135, are used to control the liquid level 140 and the interface level 145 (i.e., the level of the interface between the water level layer and emulsion layer 120). Also shown is an inlet valve 155 for the mixture inlet to the separator. The control valve on the gas outlet 150 is used to control the vessel pressure. While most of the gas separates quite easily, the emulsions are typically "tight" or stable and difficult to separate.

In general, gravity separators operate on the principle of providing adequate settling time to the immiscible phases in a relatively quiet horizontal or vertical flow. The emulsion enters the separator and based on the amount of time provided by the capacity of the separation vessel, the phases separate to varying degrees where oil can be found in the water outlet stream and water in the oil outlet stream. Oil droplets rise to the oil-water interface and water droplets settle to the interface. The emulsion layer formed between the phases retards separation. Dispersions of oil and water are complicated by the inhomogeneity of the oil and the impurities in the water.

Figure 2:
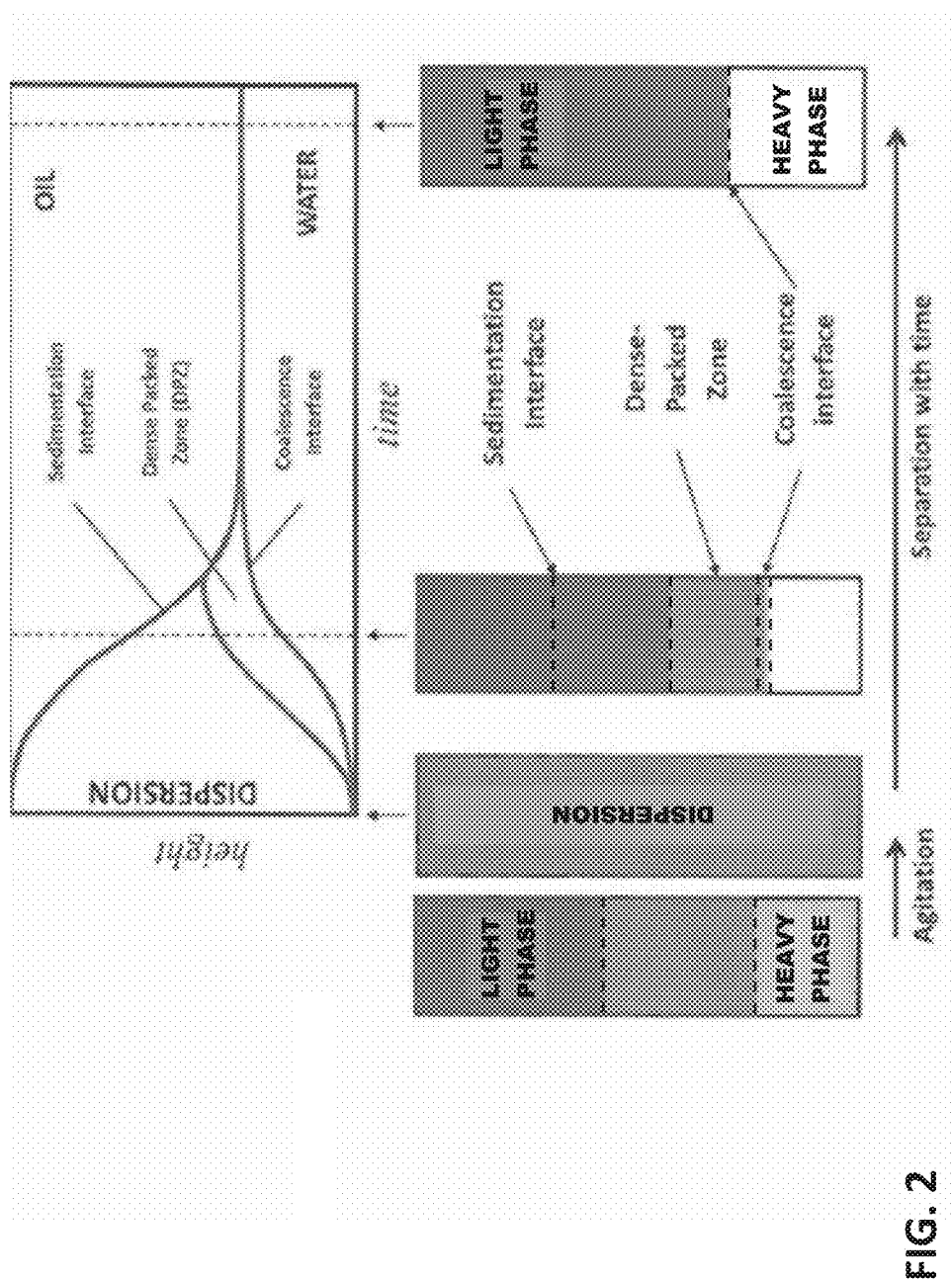
FIG. 2 is a high-level diagram illustrating the principles of two-phase liquid-liquid separation in a batch static gravity separator.

FIG. 2 is provided to describe the principles of two-phase liquid-liquid separation in a batch static gravity separator.

FIG. 2 shows a schematic of the transient evolution of the water phase fraction separating from a water-in-oil dispersion. In this simple example, which corresponds to a bottle test, the light phase (oil), heavy phase (water) and treatment chemicals are added together and shaken or mechanically agitated to form an emulsion. With the passage of time, the dehydrated oil exists above the sedimentation interface and a water homophase appears below the coalescing interface. The destabilization of the emulsion can be monitored by visual observation, or by ultrasonic techniques, or by gamma densitometry, or by nuclear magnetic resonance, or other means to measure separation of phases and the concentration gradient of the dispersed phase. During phase separation, if droplet sedimentation is faster than coalescence above the droplet-interface, the droplets accumulate in a dense-packed zone (DPZ). The droplet swarm settles into a dense emulsion in the dense pack zone as the coalescence rate is slowed. The droplet phase volume fraction increases approaching the homophase and the droplet size increases due to coalescence with neighboring droplets in the dense pack zone.

The rate of oil-water separation and throughput dictate the vessel volume, length, and diameter. The efficiency of separation for an oil-rich inlet stream is based on the fraction of water in the oil outlet stream. The separation efficiency for a water-rich inlet stream is based on the fraction of oil in the water outlet stream. It is imperative for the separation process to maximize the separation efficiency and to minimize carryover of the water-in-oil or oil-in-water to satisfy the technical and commercial conditions of the downstream operations, produced water injection and crude transport lines.

Existing systems and methods for the design and sizing of gravity separators is generally done using established techniques that are based on the retention time of fluids in the separator. The API 12J standard, for example, provides guidelines for retention time. The retention time, which is related to the vessel volume, production rate, fluid densities and fluid viscosities, determines the amount of time for oil and water separation. The retention time is selected on the basis of the separator type—two phase or three-phase separator, and the API gravity of the oil (density and viscosity of the oil). Gas-liquid separation is addressed similarly with the retention time available for droplet separation from the gas phase.

The vessel retention times for gas-liquid and liquid-liquid separation are determined from the available cross-sectional area used to determine the gas and liquid superficial velocities. The retention time is used as the principal sizing parameter in liquid-liquid separation per the API standard. The liquid capacity is selected based on a specified retention time for a specific oil gravity. Further to this method, Stokes law is used to determine the cut-off droplet size, or minimum droplet size for separation. All droplets larger are presumed separated while all droplets less that the cut-off diameter are carried over in the product stream. The droplet cut-off is typically 100 to 500 microns.

The separator vessel size is determined from the time required for the cut-off droplet to settle based on the terminal falling velocity for a single sphere in a quiescent dilute fluid, according to Stokes Law. The retention time design criteria do not take into consideration the inlet conditions, emulsion stability, droplet size distribution, internals, or the water interface level. These classic design guidelines lead to oversized designs that are costly, or unresponsive to changes in emulsion stability, or undersized and lacking the requisite efficiency.

Numerous attempts have been made to model liquid-liquid separation and the performance of horizontal gravity separators using Computational Fluid Dynamics (CFD). Previous studies show that CFD predictions help to elucidate the macroscopic parameters, like flow patterns and phase residence time, however, CFD has been unable to accurately predict liquid phase separation performance.

In accordance with one or more of the disclosed embodiments the systems and methods further described herein improve on existing CFD modeling techniques through more accurate methods of modeling the oil-water emulsion and including the dispersed phase droplet size distribution and emulsion rheology in such models.

Size distribution of the dispersed phase in liquid-liquid dispersions influences the separation kinetics. Accounting for the dispersed phase size distribution in predicting the settling behavior can improve separation models. The existing liquid-liquid dispersion separation models are based on static experiments performed in so-called bottle tests where the mixture of oil and water is prepared by homogenization. The resulting emulsion can consist of water droplets dispersed in oil or oil droplets dispersed in water, or some combination of the two, including complex emulsions, depending on the water cut (the ratio of water compared to the volume of total liquids). Immediately following the agitation, the dispersion separates with time in a tall slender cylindrical glass vessel. The bottle test is a common test used in the energy industry to determine crude emulsion stability and is a proxy for industrial-scale gravity separation units. Simply, the bottle test involves observation of oil-water phase separation with time following the initial physical agitation of the sample. There are different methods and procedures for the bottle test and is generally used as the primary method to screen demulsifying chemicals by assessing how well the demulsifiers reduce the time required to separate the water from the oil.

Existing methods for the design of separators is based on the transport of a single droplet or the average retention time of the phase to be separated. Typically, this approach does not take into account the multidimensional flow field in the separator and is prone to over-sizing the separator volume. The system and method further described herein allows the determination of the separation efficiency on the basis of the true geometry and multidimensional flow field and for a distribution of droplet sizes with the influence of the emulsion concentration on the rheology of the oil-in-water or water-in-oil dispersion.

Specific Features of the Present Invention:

According to a salient aspect, the systems and methods further described herein improve on the existing methodologies for designing gravity separators based in part on a more comprehensive and accurate simulation of the separation in gas-oil-water and oil-water in batch or continuous gravity separators to predict the separation of the liquid phases and to determine the separation efficiency. In some implementations such modeling is performed using computational fluid dynamics (CFD) software simulations. In particular, the exemplary systems and methods incorporate Eulerian multiphase modeling method or similar methods to solve for separate phases and characterize the relative or slip velocity between each of the phases in the simulation, and the population balance model or similar method to: characterize the distribution of dispersed phase droplet diameter in the simulation, characterize the evolving droplet size distribution due to droplet-droplet coalescence, and the higher viscosity dense emulsion layer that forms between the light phase dispersion and the heavy phase dispersion.

Figure 3:
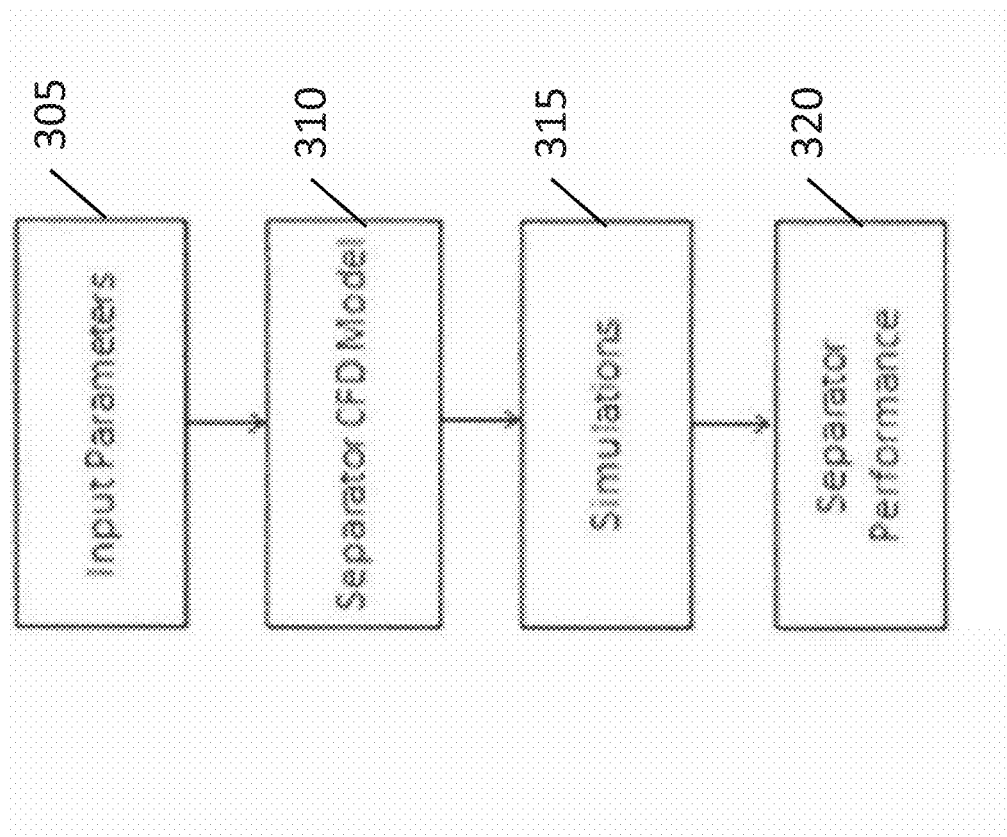
FIG. 3 is a flow diagram illustrating a method for simulating gravity separation of immiscible liquid dispersions in accordance with one or more of the disclosed embodiments.

According to one or more embodiments, the general method for simulating gravity separation of immiscible liquid dispersions follows the process illustrated in FIG. 3. The method can be executed as a computational fluid dynamics (CFD) simulation to predict the separation of phases. The routine 300 begins at step 305, where Input Parameters for the simulation are obtained and analyzed. Then at step 310, the Separator CFD model are constructed and set-up. Then at step 315, the Simulations (using a multiphase CFD approach coupled with population balance modeling) are performed. At step, 320, the post-processing of the simulation output to describe the Separator Performance is performed (including the rate of phase separation with time, and the efficiency of separation in a two- or three-phase separator). In one or more embodiments, following processing of the simulation output, the input parameters of an existing separator can be adjusted in accordance with the results of the simulation in order to optimize the liquid-liquid separation efficiency of the separator for a particular immiscible liquid dispersion composition. These adjustments allow the existing separator to separate and output one or more processed liquid streams from the immiscible liquid dispersion composition, where the processed liquid streams contain minimal amounts of the immiscible liquid dispersion. In at least one embodiment, the simulation outputs can also be used to design a new separator optimized for prevailing operating conditions.

Figure 4:
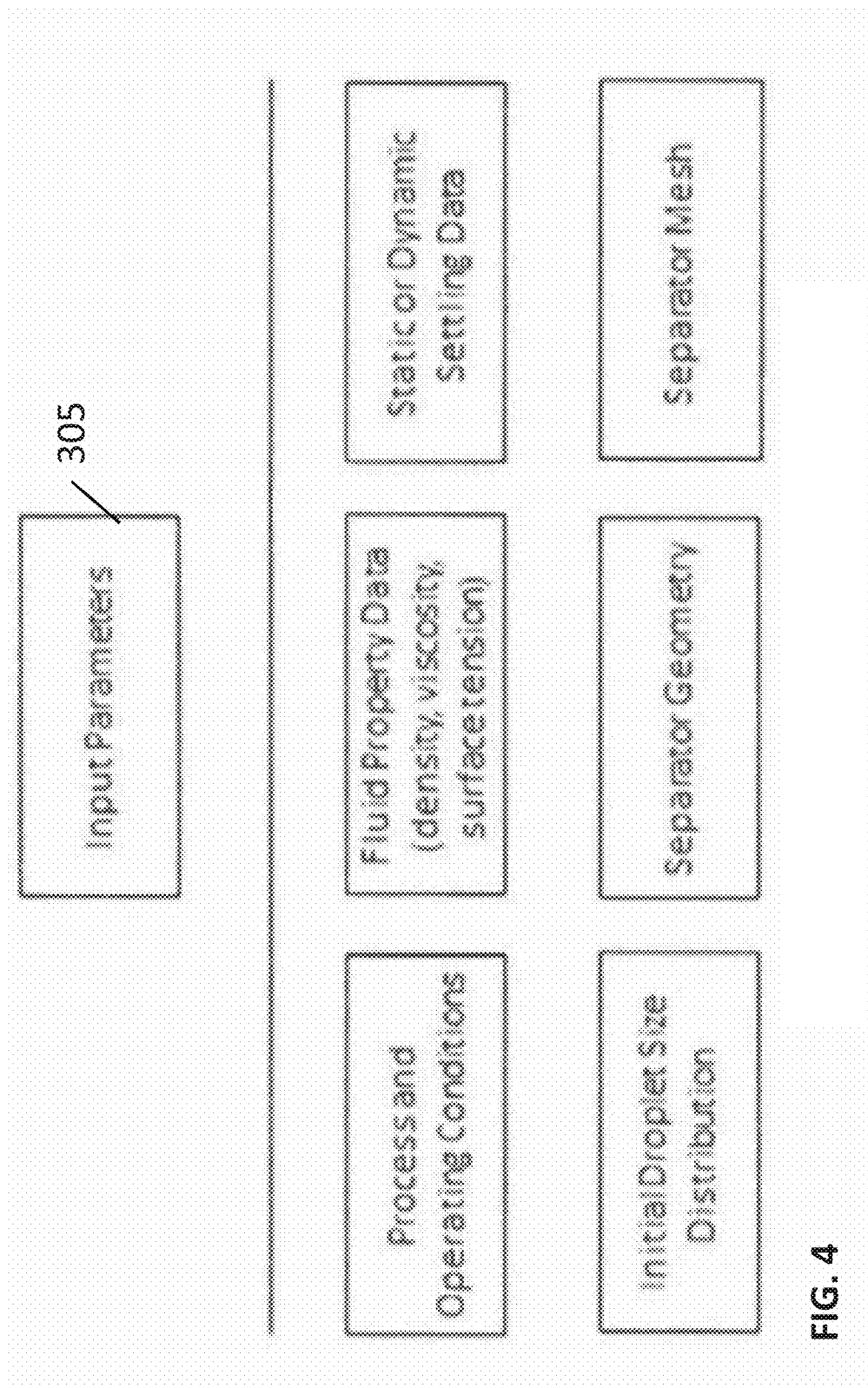
FIG. 4 is a flow diagram illustrating input parameters for the method for simulating gravity separation of immiscible liquid dispersions in accordance with one or more of the disclosed embodiments.

As shown in FIG. 4, which is a block diagram depicting the exemplary parameters that are obtained and analyzed at step 305 and used as inputs to generate the CFD model can include:
1. Process and Operating Conditions including Flow rate (for continuous separator), temperature and pressure
2. Fluid Property Data including Density, viscosity, surface tension, and treatment chemical concentration
3. Static or Dynamic Settling Data
4. Initial droplet size distribution as the initial dispersion of oil-in-water and/or water-in-oil will have a distribution of dispersed droplet
5. Separator geometry
6. Separator computational mesh.

Figure 7:
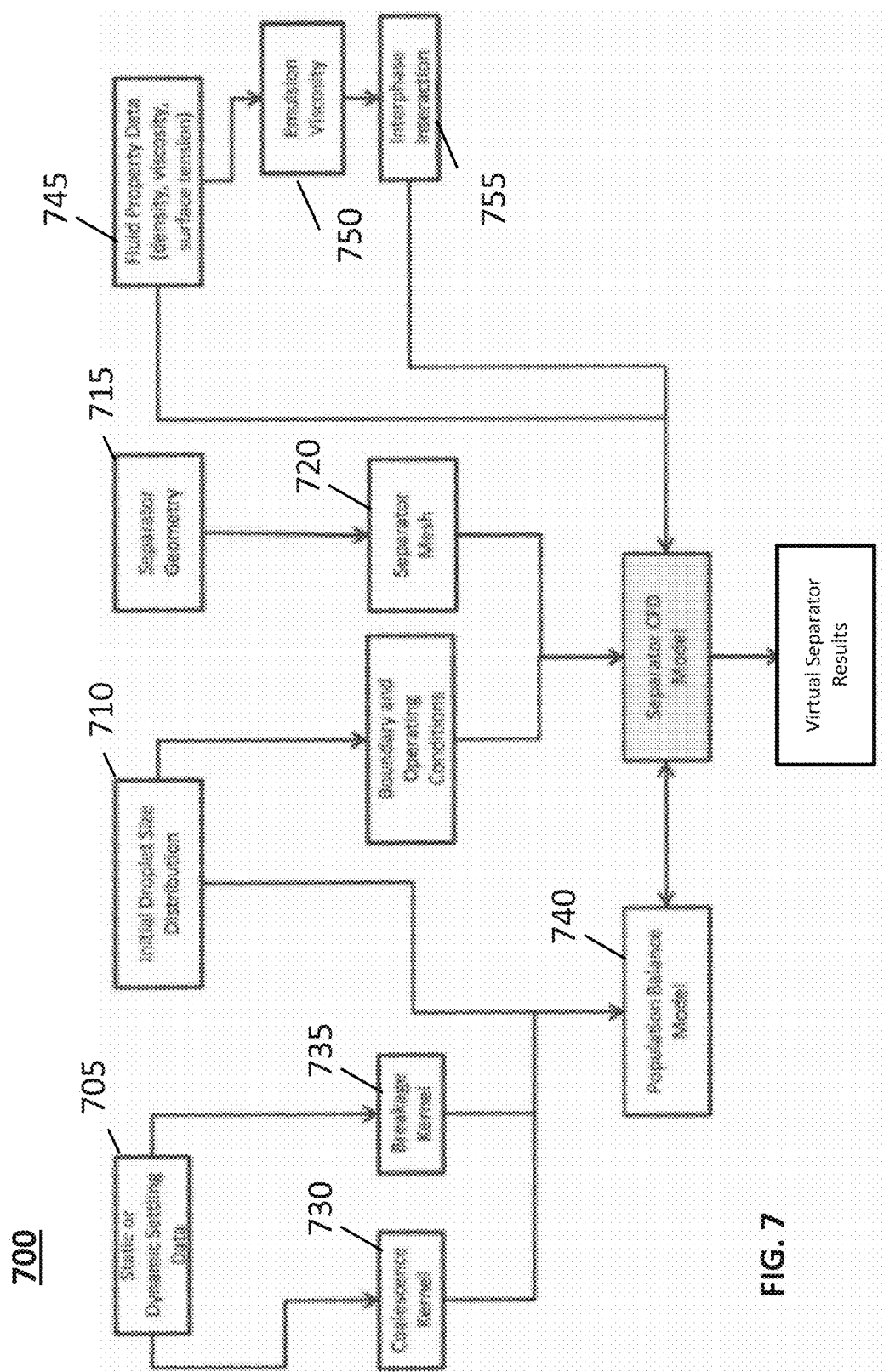
FIG. 7 is a flow diagram illustrating a method for simulating gravity separation of immiscible liquid dispersions in accordance with one or more of the disclosed embodiments.

The various steps for defining the input parameters and for generating the separator CFD Model (e.g. at steps 305 and 310 of routine 300) are further described herein and illustrated in the exemplary process flow diagram of FIG. 7.

In general, FIG. 7 depicts a process 700 that can be used in the design, simulation and control of multi-phase separator systems. The process utilizes computational fluid dynamics (CFD) software that is configured to determine the separation efficiency of separators on the basis of the true separator geometry and multidimensional flow field and for a distribution of droplet sizes with the influence of the emulsion concentration on the rheology of the oil-in-water or water-in-oil dispersion.

Specifically, the process 700 involves various inputs and computational steps for modeling a three-phase gravity separation system and it can be appreciated that the various steps described herein and depicted in the figures can be performed in a variety of different orders or combinations. At step 715, a gravity separator vessel is represented in a three-dimensional CFD simulation and the separator mesh is defined at step 720. Each of the gas, light liquid, and heavy liquid volumes in the separator is represented using an Eulerian multiphase modeling method or similar method. At step 710, the initial droplet size distribution is defined and the dispersed liquid phase droplet size distribution is represented in the CFD simulation by population balance modeling (PBM), at step 740. In particular, this distribution is modeled at step 740 by solving the population balance equation using multivariate methods (e.g., the inhomogeneous discrete method or the direct quadrature method of moments).

In addition, coalescence and breakage kernels are determined at steps 730 and 735, respectively, based on static or dynamic settling data, including the dynamic droplet size determination using Nuclear Magnetic Resonance, optical microscopy, Focused Beam Reflectance Measurement or other methods. The coalescence and breakage kernels are applied as inputs to the population balance model, at step 740, to define droplet size evolution in the population. Droplet size evolution can be a result of droplet size and additional physical properties (e.g., density, viscosity, surface tension determined at step 745), momentum or velocity, turbulence energy dissipation rate, turbulent kinetic energy, demulsifier or surfactant concentration, and other variables or gradients of variables.

At step 755, the phase interaction between the continuous and dispersed phase (i.e., between oil and water droplets) is modeled. This includes accounting for the dispersed phase fraction concentration between dilute to semi-dilute and the concentrated regimes, and the dispersed phase droplet size. In addition, interphase interaction is determined as a function of determining, at step 750, the emulsion or dispersion viscosity, which is calculated as a function of a droplet diameter factor.

The various steps of routine 700 for defining the various parameters and the CFD model are further described below.

Static or Dynamic Settling Data

As shown in FIG. 7, at step 705, Static or Dynamic Settling Data is obtained. Static or Dynamic Settling Data can include time-varying vertical profiles of phase fraction distribution and settling and coalescence profiles. This data can be obtained from static or dynamic settling data obtained using a bottle test or separator vessel or container testing. Accordingly, the profiles can be obtained from visual observation, ultrasonic measurements, gamma densitometry measurements, nuclear magnetic resonance NMR measurements, electrical tomography, or other method to determine the time-varying vertical distribution of the settling or rising phase in the separator or bottle or container. For instance, in some implementations the settling data profiles can be obtained prior to design of a separator. Moreover, during operation such information can be monitored in real time so as to adjust control parameters to so as to optimize operation and production. For example, during operation, the time varying vertical distribution can be determined by a controller computing device having a hardware processor that is configured by executing code in the form of one or more modules stored in a non-transitory storage medium. More specifically, the time varying vertical distribution can be determined by the processor using a sensor device operatively connected to the separator. Alternatively, the sensor device can be operatively connected to an inlet or outlet stream to or from the separator, like a sampling port, at the operating pressure and temperature, or at ambient pressure, or at a specified pressure, for example. The sensor is configured to take one or more of ultrasonic measurements, gamma densitometry measurements, nuclear magnetic resonance NMR measurements, electrical tomography measurements, and optical and visible measurements of the liquid dispersion.

Initial Droplet Size Distribution

In addition, at step 710, from batch separation data (the dispersed phase fraction distribution), the contour lines of constant dispersed phase fraction are extracted as a function of time. These iso-value curves of the dispersed phase fraction versus time are analyzed. The average settling droplet size is calculated from the gradient of the settling profile, that is, the rate of change of height of the iso-value curve of the mean dispersed phase concentration with time, or the settling velocity:

$$v_s = \frac{dH}{dt}$$

where H is height settled over a specified time t.

In addition, the settling velocity can be compared to the following to establish the size range of the mean settling droplet diameter;

Unhindered Settling—Stokes Law:

$$v_s = \frac{g d_d^2 (\rho_c - \rho_d)}{18 \mu_c}$$

Hindered Settling:

The water droplet settling velocity is calculated from the following relationships, for example, (Henscke, Schlieper, & Pfennig, 2002):

$$Re = \frac{3 q \varepsilon_0}{c_w \xi (1 - \varepsilon_0)} \left[ \left( 1 + Ar \frac{c_w \xi (1 - \varepsilon_0)^3}{54 q^2 \varepsilon_0^2} \right)^{0.5} - 1 \right]$$

Where:

$$Re = \frac{\rho_c v_s d_d}{\mu_c}$$

$$Ar = \frac{\rho_c \Delta \rho g d_d^3}{\mu_c^2}$$

$$\xi = 5 K_{HR}^{-3/2} \left( \frac{\varepsilon_0}{1 - \varepsilon_0} \right)^{0.45}$$

$$K_{HR} = \frac{3(\mu_c + \mu_d)}{2\mu_c + 3\mu_d} \left[ \left( 1 + Ar \frac{c_w \xi (1 - \varepsilon_0)^3}{54 q^2 \varepsilon_0^2} \right)^{0.5} - 1 \right]$$

$$q = \frac{1 - \varepsilon_0}{2 \varepsilon_0 K_{HR}} \exp\left( \frac{2.5 \varepsilon_0}{1 - 0.61 \varepsilon_0} \right)$$

$$c_w = \frac{Ar}{6 Re_\infty^2} - \frac{3}{K_{HR} Re_\infty}$$

$$Re_\infty = \frac{\rho_c v_\infty d_d}{\mu_c} = 9.72[(1 + 0.01 Ar)^{4/7} - 1]$$

The settling velocity v is calculated for a given droplet Sauter diameter $d_d$ and phase fraction o.

Alternatively, the Richardson-Zaki Correlation can also be evaluated for comparison:

$$v_s = v_{Stokes}(1 - \varphi_d)^n$$ where n is between 5-6.5.

The average droplet diameter is used in the selection of the emulsion viscosity model and to fit through statistical analysis, or goodness of fit, the coalescence parameters in the population balance model. The droplet size distribution can be measured at vertical intervals during settling to allow for more direct adjustment and optimization of the coalescence rate empirical parameters.

The separator inlet Droplet Size Distribution is obtained from empirical correlations or experimental measurements and gives the CFD simulation the initial droplet diameter distribution and phase fractions for each bin, or probability distribution function defined by the probability distribution of droplets in terms of the volume fraction divided by the droplet diameter.

Separator Geometry and Mesh

The geometrical information for the two-phase or three-phase horizontal or vertical separator can be obtained from design specifications of existing or proposed separator designs. At step 715, such information is used to construct the two- or three-dimensional CAD geometry of the Separator CFD Model.

In addition, at step 720, the computational mesh or grid (e.g., polygonal mesh) is constructed from the detailed separator geometry that can include internal geometric components, internals, such as inlet devices, perforated plates, baffles, vortex breakers, weirs, coalescer packs, or any other physical device obstructing or partially obstructing the flow of gas and liquid.

As shown in FIG. 7, the static or dynamic settling data provides inputs to the coalescence and breakage kernels defined at steps 730 and 735, respectively, for the population balance equation closure terms describing coalescence and breakage of the dispersed phase droplets.

The Separator CFD model can be set up with a multiphase modeling approach. The Eulerian multiphase modeling approach can be appropriate to describe complex phase rheology, phase separation and inversion in oil-water emulsions that exist in continuous and batch separators since each phase has a unique velocity or momentum field. In the multi-fluid Eulerian multiphase approach, phases are treated as interpenetrating continua where the phase volume fractions sum to one in any cell in the domain. A separate set of momentum equations and continuity equations can be solved for each phase. Interphase coupling can be modeled through pressure and momentum exchange coefficients. The Eulerian model can be applied from dispersed to dense multiphase flows with the appropriate closure achieved through constitutive models. The conservation equations are derived by ensemble averaging the local instantaneous balance for each phase. The continuity equation for phase j is $$\frac{\partial}{\partial t}(\alpha_j \rho_j) + \nabla \cdot (\alpha_j \rho_j \vec{v}_j) = \sum_{i=1}^{n} (\dot{m}_{ij} - \dot{m}_{ji})$$

where $\alpha_j$, $\rho_j$ and $\vec{v}_j$ are the phase volume fraction, density and velocity, and $\dot{m}$ is the mass transferred between phases. The momentum balance for phase j is $$\frac{\partial}{\partial t}(\alpha_j \rho_j \vec{v}_j) + \nabla \cdot (\alpha_j \rho_j \vec{v}_j \vec{v}_j) =$$

$$-\alpha_j \nabla p + \nabla \cdot \alpha_j \mu_j \left[ (\nabla \vec{v}_j + \nabla \vec{v}_j^T) - \frac{2}{3} \nabla \cdot \vec{v}_j I \right] +$$

$$\sum_{i=1}^{n} (K_{ij}(\vec{v}_i - \vec{v}_j) + \dot{m}_{ij} \vec{v}_{ij} - \dot{m}_{ji} \vec{v}_{ji}) + \alpha_j \rho_j \vec{g}$$

where ρ is pressure, μ is viscosity, I is the unit tensor, and Kij(=Kji) is the mean interphase momentum exchange coefficient and can be written in general form as:

$$K_{ij} = \frac{\alpha_i \rho_j f}{\tau_j}$$

The terms f and $\tau_j$ are the drag function and particle relaxation time, respectively, expressed as $$f = \frac{C_D Re}{24}$$

and, $$\tau = \frac{\rho_j d_j^2}{18\mu_i}$$

where $d_j$ is the Sauter mean diameter that couples the momentum equations to the population balance equation.

For settling or rising droplets, the drag originates from viscous surface shear and the pressure distribution or from drag around the droplet. For dilute dispersions, the droplets can settle or rise without interacting with neighbor droplets. For small droplets in the viscous regime, the Stokes law determines the terminal velocity in dilute or unhindered conditions. The spherical assumption makes the selection of a drag formulation more straightforward. The non-deforming assumption is also the basis for the emulsion rheology models and for the droplet collision mechanics for coalescence. In the dense dispersions found in oil-water batch and continuous gravity settling, the drag function preferably includes the influence of neighbor droplets.

The influence of neighbor droplets hinders settling. Approaches to dealing with hindered settling for liquid-liquid separation are numerous. An exemplary approach employed in multi-fluid multiphase modeling is to account for the hindered settling through modification of the single particle drag coefficient. The drag function is dependent on the dimensionless drag coefficient, phase properties and droplet diameter. The Schiller-Naumann correlation for drag coefficient $C_D$ is modified for dense suspensions using a mixture or emulsion Reynolds number $Re_m$ based on the emulsion viscosity $\mu_m$ below:

$$C_D = \frac{24}{Re_m}(1 + 0.15 Re_m^{0.687})$$

$$Re_m = \frac{\rho_c |u_d - u_c| d_d}{\mu_m}$$

The subscripts c and d refer to the continuous and dispersed phases, respectively. The drag force is the only contribution to the interphase interaction modeled. Other forces including virtual mass force, transverse lift force, or wall lubrication force may be added, but are generally not important given the low droplet Reynolds numbers of the order 0.01 for water-in-oil dispersions relevant to crude oil separation. The turbulent dispersion force contributes to diffusion in dispersed flows was not considered due to the dense phase fraction in gravity settling and low turbulence. Turbulence decay is modeled with the standard k-ε turbulence model extended to multiphase flows with or without turbulence interaction or source terms in the k and ε equations. The mixture or emulsion viscosity $\mu_m$ depends on the viscosities of the dispersed and continuous phases, the concentration of the dispersed phase, the shear field, the droplet size distribution, temperature, and the emulsion stability. The interfacial stability can be dependent on many non-hydrodynamic factors including the crude oil heavy fraction, solids, temperature, droplet size and distribution, pH, salinity, and composition. The presence of demulsifiers inhibits internal droplet circulation and the emulsion viscosity models derived for solid particle suspensions are applicable.

As the viscosity of the continuous phase increases, the collision frequency decreases lowering the coalescence and increasing the number of droplets in the emulsion. The dispersed phase concentration increases the interaction between droplets and the continuous flow field and between droplets and it is the most important factor in the crude oil emulsion viscosity. One of the main theoretical approaches used to derive equations to predict the emulsion viscosity at high concentrations is the differential effective medium theory (Bullard, Pauli, Garboczi, & Marys, 2009). Brinkman derived the following equation for emulsion viscosity for suspensions of hard spheres (Brinkman, 1952):

$$\mu_m = \mu_c (1-\varphi_d)^{-2.5} \tag{8}$$

Krieger and Dougherty extended Brinkman's correlation by including the contribution of the maximum packing value (Krieger & Dougherty, 1959):

$$\mu_m = \mu_c \left(1 - \frac{\varphi_d}{\varphi_{max}}\right)^{-2.5\varphi_{max}} \tag{9}$$

Where $\varphi_{max}$ is the maximum packing value of 0.64 for hard spheres in non-equilibrium reaching the limit of 0.74 for a hexagonal close packed structure. With increased pressure, droplets can deform and the maximum packing value $\varphi_{max}$ approaches unity. Ishii and Zuber extended the Krieger-Dougherty correlation by including a viscosity factor in the exponent (Ishii & Zuber, 1979):

$$\mu_m = \mu_c \left(1 - \frac{\varphi_d}{\varphi_{max}}\right)^{-2.5\varphi_{max}\mu_*} \tag{10}$$

$$\mu_* = \left(\frac{\mu_d + 0.4\mu_c}{\mu_d + \mu_c}\right) \tag{11}$$

The following is the Taylor equation for the viscosity of a dilute emulsion of spherical droplets (Taylor, 1932):

$$\mu_m = \mu_c \left(1 + \frac{(2 + 5\mu_d/\mu_c)}{2(1 + \mu_d/\mu_c)}\varphi_d\right) \tag{12}$$

Pal proposed the following equation incorporating crowding and the packing limit of undeformed droplets (Pal, 2011):

$$\mu_m \left[\frac{2\mu_m + 5\mu_d/\mu_c}{2 + 5\mu_d/\mu_c}\right]^{3/2} = \exp\left(\frac{2.5\varphi_d}{1 - \varphi_d/\varphi_{max}}\right) \tag{13}$$

where $\varphi_{max}$=0.64. Mills derived the following equation for the apparent shear viscosity of a concentrated suspension of hard spheres in a Newtonian fluid based on a free cell model (Mills, 1985):

$$\mu_m = \mu_c \frac{1-\varphi_d}{(1 - \varphi_d/\varphi_{max})^2} \tag{14}$$

where $\varphi_{max}$ is 0.64. The relative viscosity of an emulsion of Arab Light crude oil and brine water (50 g/L NaCl) at 45°

Figure 5:
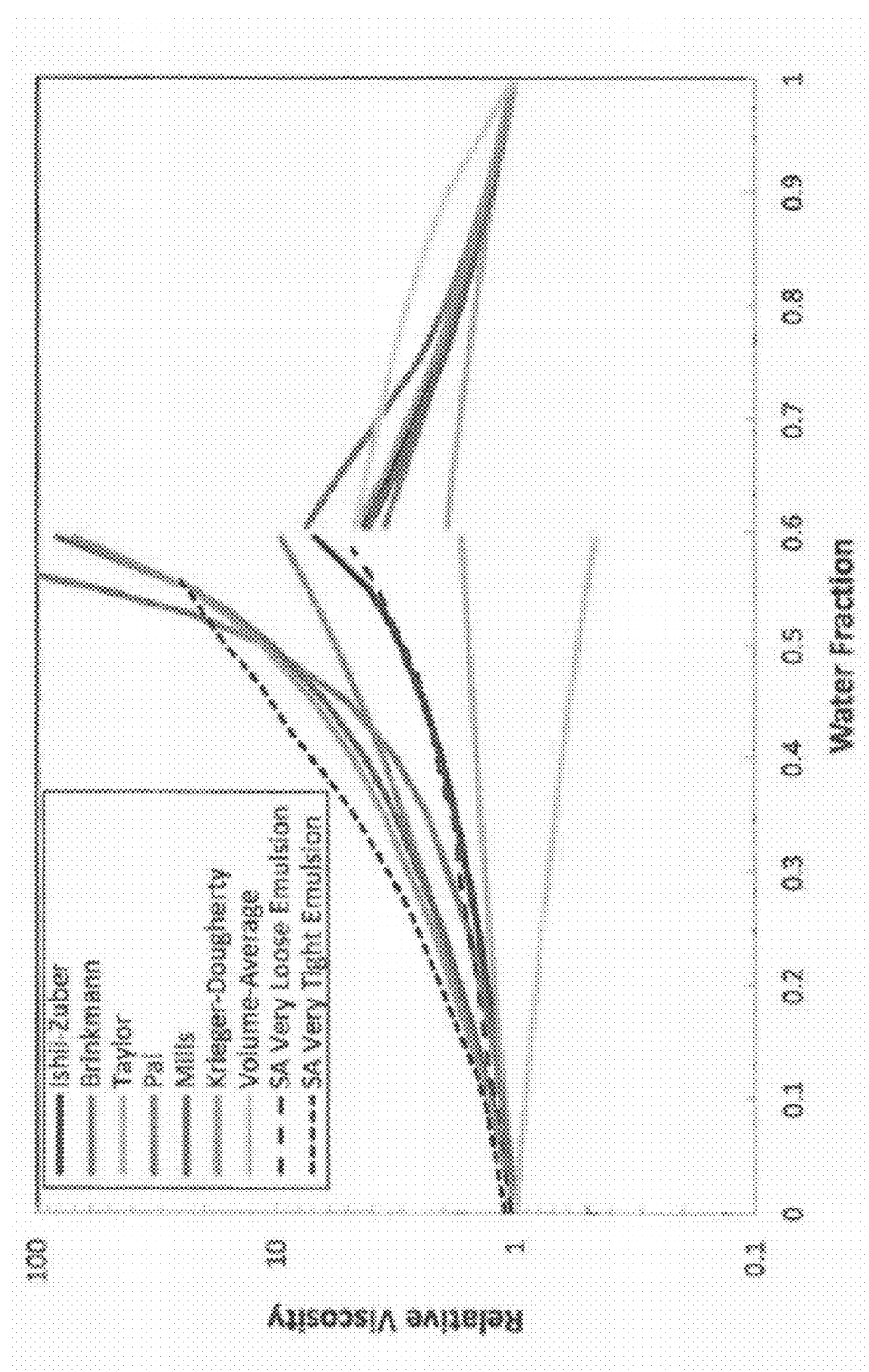
FIG. 5 is a graph illustrating the relative viscosity of an emulsion of Arab Light crude oil and brine water plotted over the range of water fraction from zero to one in accordance with one or more of the disclosed embodiments.

C. is plotted in FIG. 5 over the range of water fraction from zero to one from the emulsion correlations (Equations 8-14). Saudi Arabian loose and tight emulsions are shown for reference. The inversion point is a water fraction of 0.6.

Figure 6:
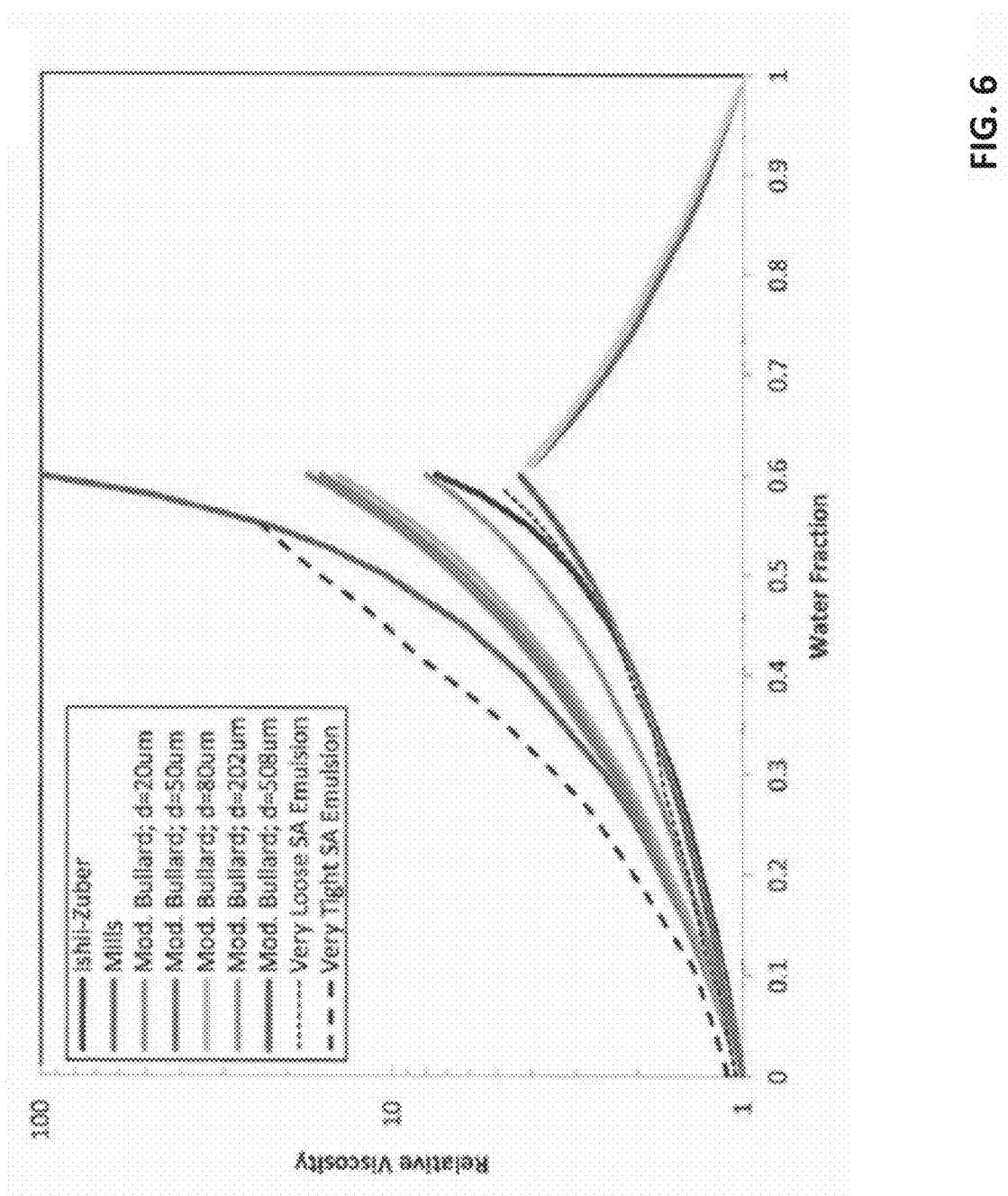
FIG. 6 illustrates an exemplary graphical output from modeling emulsion viscosity with undeformable spherical droplets in the semi-dilute and concentrated regimes with a dependence on the local droplet size in accordance with one or more of the disclosed embodiments.

In view of the foregoing, at step 750, the exemplary systems can apply the following relationship for modeling the emulsion viscosity with undeformable spherical droplets in the semi-dilute and concentrated regimes with a dependence on the local droplet size (plotted in FIG. 6):

$$\mu_m = \mu_c \left(1 - \frac{\varphi_d}{\varphi_{max}}\right)^{-2} \left[1 + C_1\left(\frac{\varphi_d}{\varphi_{max}}\right) + C_2\left(\frac{\varphi_d}{\varphi_{max}}\right)^2\right]$$

Where $$C_1 = [\eta]\varphi_{max} - 2$$

$$C_2 = k_H \varphi_{max}^2 - 2[\eta]\varphi_{max} + 1$$

$$[\eta] = \frac{1 + z[\eta]_\infty}{1 + z}$$

$$[\eta]_\infty = 2.5$$

$$k_H = \frac{1}{2}[\eta]([\eta] + K)$$

$$K = \frac{1}{\varphi_{max}}$$

$$z = \frac{\mu_d}{\mu_c} d^*$$

$$d^* = \zeta \exp(-\lambda d_d)$$

According to a salient aspect, the addition of the diameter factor d* is an improvement to existing systems and methods for the calculation of emulsion viscosity.

A distribution specific to the particle, bubble or droplet population is modeled with the population balance equation at step 740. A population balance equation is coupled with the turbulent multiphase momentum equations and conveniently describes the droplet size distribution (Ramkrishna, 2000). The general population balance equation is written as a continuity statement of the droplet number density function:

$$\frac{\partial}{\partial t}[n(V, t)] + \nabla \cdot [\vec{v}n(V, t)] = S(V, t) \quad (15)$$

The spatial location of the particle is an "external coordinate" in the particle state vector while the droplet volume V is an "internal coordinate" of the population distribution. The source term S(V, t) for breakage b and coalescence c due to birth (B) and death (D) rates is further expanded as:

$$S(V,t) = B_b(V,t) - D_b(V,t) + B_c(V,t) - D_c(V,t) \quad (16)$$

The closure of Equation (15) requires a derivation of the source terms in Equation (16) above.

The breakage rate kernel is the product of the breakage frequency g (V') and the probability density function β (V|V') of droplets breaking from volume V' to V. The birth rate of droplets of volume V due to breakage is $$B_b = \int_{\Omega_V} p g(V') \beta(V | V') n(V') dV' \quad (17)$$

where g(V') n(V') dV' droplets of volume V' break per unit time, producing for p child droplets, p g(V') n(V') droplets of which a fraction β(V|V')dV represents droplets of volume V (ANSYS Inc., 2012). The breakage PDF β(V|V') is also referred to as the daughter size distribution function where the fragments or daughter droplet mass must equal the original droplet mass. The death rate of droplets is $$D_b = g(V)n(V) \quad (18)$$

There are several different models for determining the breakage frequency and the breakage PDF to compute the breakage rate of the droplets. The coalescence kernel α(V−V', V') is a product of the collision frequency h(V−V', V') between droplets of volume V and V', and the coalescence efficiency λ(V−V', V'). The coalescence efficiency is the probability that droplets of volume V will coalesce with droplets of volume V'. The birth rate of droplets due to coalescence is $$B_c = \frac{1}{2}\int_0^V a(V - V', V') n(V - V') n(V') dV' \quad (19)$$

The death rate of droplets due to coalescence is $$D_c = \frac{1}{2}\int_0^V a(V, V') n(V) n(V') dV' \quad (20)$$

The droplet breakage and coalescence kernels describe the evolution of the droplet size distribution during phase separation. The droplet breakage and coalescence kernels are system dependent and can be selected based on the system requirements.

There are several approaches to solving the population balance equation. In gravity separation in a shear field, the droplet phase advection is driven strongly by the droplet size. The droplet size and volume fraction distributions establish the droplet settling velocity field. All the droplets in the population cannot share the same velocity field. In the separation of the continuous phase from the dispersed phase(s), droplets of different sizes will rise or settle at different velocities. The droplet size distribution can range over two to three orders of magnitude and the distribution can be mono- or multimodal. Multivariate methods incorporating several velocity classes are required to model this tight coupling between the droplet size distribution and the secondary phase velocity distribution, e.g., the Direct Quadrature Method of Moments (Marchisio & Fox, 2005) and the Inhomogeneous Discrete Method (Frank, Zwart, Shi, Krepper, Lucas, & Rohde, 2005; Sanyal, Ozarkar, & Liu, 2013). The number of velocity groups and sub-bins represents the dispersed phase droplet diameter distribution. A true discretization of the distribution would require a very large number of velocity groups. More velocity groups would be required for a multimodal or broad droplet size distribution compared to a narrow, mono-modal distribution. By increasing the number of velocity groups, the resolution of the axial water fraction profile is improved. As the number of velocity groups increases, there is less difference in the settling rate of each velocity group. With the Inhomogeneous Discrete Method, more than six velocity groups would typically be required to resolve the separation profiles for oil-water emulsions. The DQMOM does not capture the range of separation profiles compared with IDM (velocity groups >6) because only three quadrature points are possible without introducing excessive numerical error. The initial droplet size distribution is used in the population balance model to define the initial distribution of the dispersed droplet phase.

The initial droplet size distribution is also used to specify the initial distribution of secondary phase fractions for each bin or quadrature point at the inlet to the continuous separator and in batch separation for the initial distribution of the secondary phase fractions.

The fluid property data along with the static/dynamic settling data is used to determine the emulsion viscosity model implemented through the interphase interaction in the multiphase model.

All aforementioned information and data are input to the separator CFD model from which virtual separator results can be analyzed and the separation performance of the batch or continuous separator can be assessed.

Figure 8:
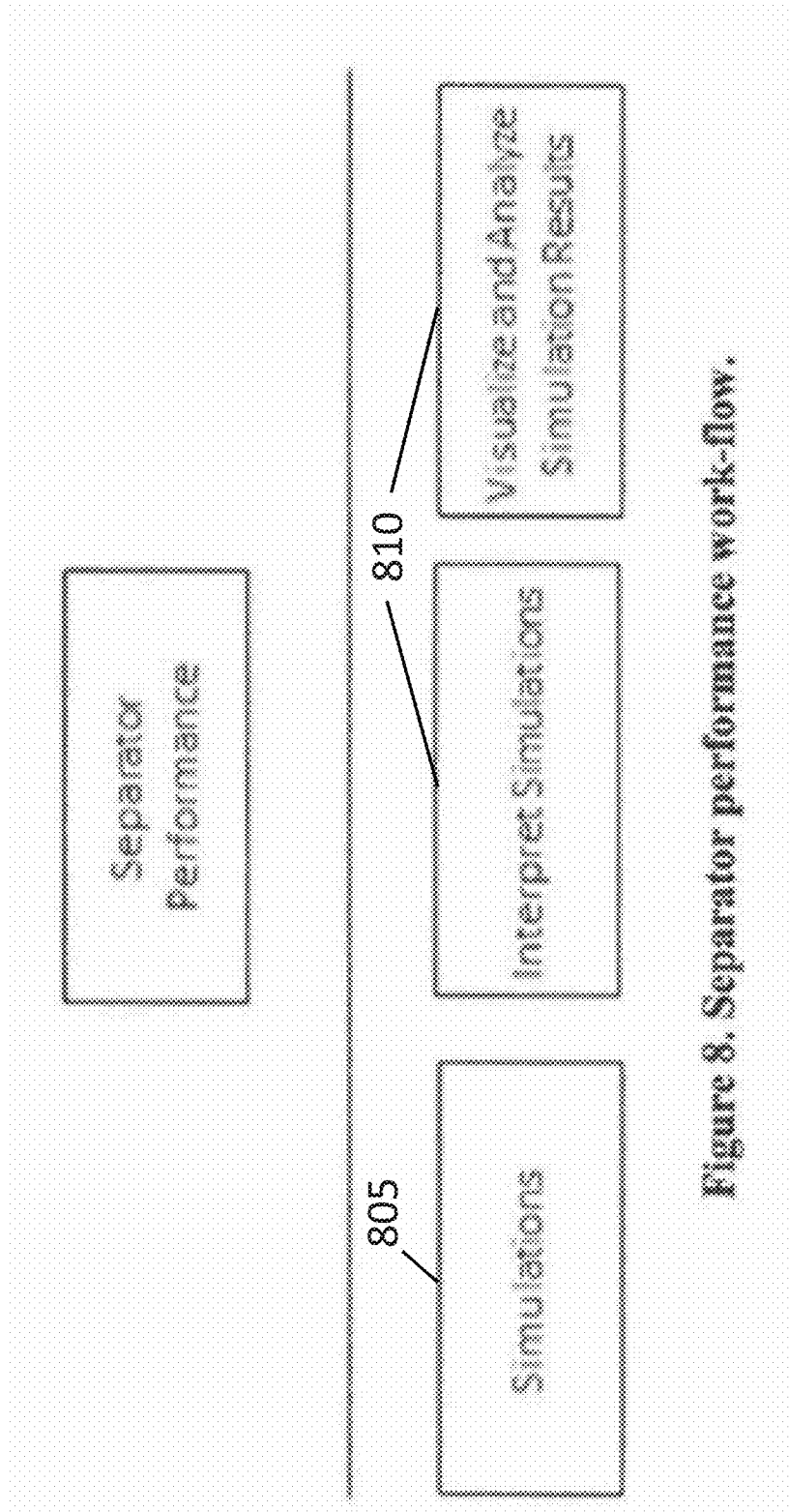
FIG. 8 is a flow diagram illustrating a method for assessing the separator performance for the separator CFD model in accordance with one or more of the disclosed embodiments.

FIG. 8 describes the process flow diagram for assessing the separator performance for the separator CFD model. At step 805, simulations are performed using the separator CFD model. At step 810, the simulation results are generated and assessed to determine the distributions of all phases in the separators, and the variation of phase velocity, viscosity, droplet size distribution, and retention time of each phase. From the simulated phase composition in the outlet streams, the separation efficiency of the model separator can be determined, for instance according to the following equation:

Water Separation Efficiency=(Flow Rate of Water In at Inlet−Flow Rate of Water out at Water Outlet)/Flow Rate of Water In at Inlet.

The CFD simulation data consists of distributions of velocity, phase concentration, turbulence, viscosity, droplet diameter and other variables throughout the separator. This data can be visualized using vector plots, contour plots, stream line plots, and/or two- or three-dimensional profile plots and output using an associated display. In addition, the simulation data can be further analyzed using the computing device. For example, the simulation data allows the comparison of the flow and velocity distributions of the different phases throughout the vessel and the interaction and effect of internals in the inlet region or the separation region or the outlet region of the separator. The simulation is also used to determine the residence or retention time of the gas, oil, water phases, and the emulsion as is dictated by the specific internal geometry of the separators. The simulation data can be used to determine the beneficial performance of different internal components and determine the optimal arrangement and design of internals used to optimize separation of oil and water, and gas and liquid. The simulation can also show the development of the emulsion band and the effect of the emulsion band thickness on the oil-water separation performance.

In one or more embodiments, the CFD model of the present application is shown to qualitatively reproduce physical (ultrasound measurements) experiments/observation. This is exemplified by FIGS. 9A-B, which show graphs illustrating the height fraction over time for the water fractions using the modified Bullard model (9A) and the ultrasonic technique (9B) in accordance with one or more of the disclosed embodiments. More specifically, FIG. 9A is the CFD solution to the experimental observation shown in FIG. 9B.

As mentioned above, the present application also relates to systems for the separation of immiscible liquid dispersions. An exemplary embodiment of the system for the separation of immiscible liquid dispersions is shown at FIG. 10, including hardware components. Specifically, system 1000 includes at least one controller computing device 1005 having a processor 1010, and one or more separators 1015. The methods discussed above can be accomplished in whole or in part using system 1000, as described in further detail below.

As would be understood by those in the art, the controller computing device 1005 can include functional hardware components specifically designed to facilitate performing operational tasks, including providing certain input parameters to one or more separators 1015. Controller computing device 1005 can also include electronic circuitry that includes a memory and/or computer readable storage medium which are configured to store information relating to the operation of the controller computing device 1005 and/or separator 1015 such as configuration settings and one or more control programs.

More specifically, the controller computing device 1005 can be arranged with various hardware and software components that serve to enable operation of the system, including a processor 1010, a memory 1020, a sensor 1040, a communication interface 1050 and a computer readable storage medium 1090. The processor 1010 serves to execute software instructions that can be loaded into the memory 1020. The processor 1010 can be a number of processors, a multi-processor core, or some other type of processor, depending on the particular implementation. In one or more embodiments, the one or more separators 1015 can also comprise various hardware and software components (e.g., processor, memory, communication interface).

Preferably, the memory 1020 and/or the storage 1090 are accessible by the processor 1010, thereby enabling the processor 1010 to receive and execute instructions stored on the memory 1020 and/or on the storage 1090. The memory 1020 can be, for example, a random access memory (RAM) or any other suitable volatile or non-volatile computer readable storage medium. In addition, the memory 1020 can be fixed or removable. The storage 1090 can take various forms, depending on the particular implementation. For example, the storage 1090 can contain one or more components or devices such as a hard drive, a flash memory, a rewritable optical disk, a rewritable magnetic tape, or some combination of the above. The storage 1090 also can be fixed or removable or remote such as cloud based data storage systems.

One or more software modules 1030 are encoded in the storage 1090 and/or in the memory 1020. The software modules 1030 can comprise one or more software programs or applications having computer program code or a set of instructions executed in the processor 1010. Such computer program code or instructions for carrying out operations and implementing aspects of the systems and methods disclosed herein can be written in any combination of one or more programming languages. The program code can execute entirely on controller computing device 1005, as a stand-alone software package, partly on the controller computing device 1005 and partly on a remote computer/device or entirely on such remote computers/devices. In the latter scenario, the remote computer systems can be connected to controller computing device 1005 through any type of network, including a local area network (LAN) or a wide area network (WAN), or the connection can be made through an external computer (for example, through the Internet using an Internet Service Provider).

Preferably, included among the software modules 1030 are a database module 1070, an input parameters module 1072, a CFD model generator module 1074, an adjustment module 1076, and a simulation module 1078, are executed by processor 1010. During execution of the software modules 1030, the processor 1010 is configured to perform various operations relating to the configuration of the controller computing device 1005, as will be described in greater detail below. In addition, it should be noted that other information and/or data relevant to the operation of the present systems and methods can also be stored on the storage 1090, for instance various control programs 1060 used in the configuration of the controller computing device 1005.

A database 1080 can also be stored on the storage 1090. Database 1080 can contain and/or maintain various data items and elements that are utilized throughout the various operations of the system 1000. Preferably, some or all of the stored information in the database 1080 can be actionable data that is in a form or can be transformed into a form that enables the controller computing device 1005 to undertake an action as needed by the program that implements any given application. The database 1080 can also include device-specific applications that, when executed by the processor 1010, configure the processor to communicate with the one or separators 1015. Similarly, the database can store other operational parameters that are specific to the controller computing device 1005 and/or separator(s) 1015.

It should be noted that although database 1080 is depicted as being configured locally to the storage of the controller computing device 1005, in certain implementations, database 1080 and/or various of the data elements stored therein can be located remotely (such as on a remote server—not shown) and connected to the controller computing device 1005 through a network in a manner known to those of ordinary skill in the art.

A communication interface 1050 is also operatively connected to the processor 1010 and can be any interface that enables communication between the controller computing device 1005 and external devices, machines and/or elements such as the separator(s) 1015. Preferably, the communication interface 1050 includes, but is not limited to, a modem, a Network Interface Card (NIC), an integrated network interface, a radio frequency transmitter/receiver (e.g., Bluetooth, cellular, NFC), a satellite communication transmitter/receiver, an infrared port, a USB connection, and/or any other such interfaces for connecting controller computing device 1005 to other computing devices and/or communication networks, such as private networks and the Internet. Such connections can include a wired connection or a wireless connection (e.g., using the IEEE 802.11 standard) though it should be understood that communication interface 1050 can be practically any interface that enables communication to/from the controller computing device 1005.

As mentioned above, the methods of the present application can be accomplished in whole or in part, using the system 1000, and in particular the controller computing device 1005.

Specifically, referring again to FIG. 7, at steps 705-710, the processor 1010, which is configured by executing one or more of the software modules 1030 including input parameters module 1072, receives and analyzes operational input parameters for the separator 1015. In one or more embodiments, the operational input parameters can include fluid property data for the immiscible liquid dispersion (e.g., density, viscosity and surface tension) static or dynamic settling data for the immiscible liquid dispersion, and geometry of an internal volume of the separator including one or more internal geometric components therein. In one or more embodiments, the processor 1010 can receive one or more of the operational input parameters via user input or, alternatively, the processor 1010 can be configured to retrieve one or more operation input parameters from the database 1080 (e.g., by executing database module 1070). In at least one embodiment, the processor 1010 can receive one or more of the operational input parameters from the processor of a separator 1015 (e.g., over a Network), where the input parameters (e.g., fluid property data) are determined via real-time monitoring of the immiscible liquid dispersion in the separator 1015. For instance, a multi-liquid and multiphase immiscible liquid dispersion (e.g., having gas, oil, and water phases) can be provided to the separator 1015 and the processor of the separator 1015 can be configured to analyze the fluid properties of the immiscible liquid dispersion and transmit the resulting data to the computing device 1005 (e.g., over a network). The processor of the separator 1015 can also transmit data regarding the geometry of the separator, including one or more internal geometric components, to the computing device 1005. The processor 1010, executing one or more of the software modules 1030 including input parameters module 1072, can then analyze the received operational input parameters.

At steps 710-755, the processor 1010, configured by executing one or more of the software modules 1030 including modules database module 1070, input parameters module 1072, and CFD model generator module 1074, generates a computational fluid dynamics (CFD) model of the separator including the immiscible liquid dispersion based on the input parameters. For example, in one or more embodiments, the steps of generating the CFD model includes: defining, based on the geometric input parameters, a three-dimensional geometric model of the internal volume of the separator and its internal components therein (step 715); defining, based on the three-dimensional model, a computational mesh for the internal volume of the separator (step 720); determining, an initial droplet size distribution of the immiscible liquid dispersion (step 710); representing volumes for each of a continuous gas phase, a heavier liquid phase and a lighter liquid phase within the interior volume of the separator (e.g., using a Eulerian multiphase model); representing, for a volume of a dispersed liquid phase, a droplet size distribution with population balance modeling, such that the distribution is modeled by solving a population balance equation according to multivariate methods (step 740); and applying coalescence and breakage kernels to model droplet size evolution in the population as a function of droplet size and the fluid property data (steps 730, 735, 745). Finally, the step of generating the CFD model concludes with modeling the phase interaction between each of the continuous liquid phases and the dispersed liquid phase, wherein the model of the phase interaction is a function of the dispersed phase fraction concentration between dilute, semi-dilute and concentrated regimes within the dispersed liquid phase volume and is a function of a dispersed phase droplet diameter and a dispersion viscosity (steps 750 and 755).

Referring now to FIG. 8, at step 805, the processor 1010, configured by executing one or more of the software modules 1030, including simulation module 1078, performs one or more simulations using the generated CFD model. At step 810, the processor 1010, configured by executing one or more of the software modules 1030, including simulation module 1078, simulation results are generated and assessed to determine the distributions of all phases in the separators, and the variation of phase velocity, viscosity, droplet size distribution, and retention time of each phase. From the simulated phase composition in the outlet streams, the separation efficiency of the model separator can be determined.

In one or more embodiments, based on the CFD model simulation results, the processor 1010, executing one or more of the software modules 1030, including adjustment module 1076, can adjust one or more of the operational input parameters of the separator 1015 to maximize the liquid-liquid separation efficiency. For example, the processor 1010, executing one or more of the software modules 1030, including adjustment module 1076 and input parameters module 1072, can send a signal (e.g., via communication interface 1050 over a network) to the separator 1015 (e.g., received by the separator at a receiver), which causes the separator 1015 to adjust one or more of the operational input parameters for the separator 1015. This adjustment of one or more of the operational input parameters of the separator 1015, based on the assessment of the simulation results, can maximize the liquid-liquid separation efficiency of the separator 1015 for the particular immiscible liquid dispersion provided to the separator (the same immiscible liquid dispersion included in the CFD model).

Finally, in one or more embodiments, the processor 1010, executing one or more of the software modules 1030, can cause the separator 1015 to run using the adjusted input parameters for the particular immiscible liquid dispersion provided to the separator, which results in the outputting of one or more streams of processed liquids separated from the immiscible liquid dispersion and containing minimal amounts of the immiscible liquid dispersion (i.e., maximized liquid-liquid separation efficiency). For example, the processor 1010, executing one or more of the software modules 1030, can send a signal (e.g., via communication interface 1050 over a network) to the separator 1015, which causes the separator 1015 to run using the adjusted input parameters. In an alternative embodiment, the separator 1015 can be automatically configured to run upon receiving the signal to adjust the input parameters. In one or more embodiments, the input parameters can be adjusted before, during, and/or after the separator has begun running with a particular immiscible liquid dispersion.

In view of the foregoing, it can be appreciated that the foregoing exemplary embodiments present a methodology for CFD simulation of 2- or 3-phase separators that include algorithms for predicting the liquid-liquid separation efficiency. In particular, the proposed systems and methods are configured to model multi-phase separators based on evaluation of the emulsion viscosity and implement the emulsion viscosity formulation through the interphase drag for multi-fluid, multiphase CFD simulations of batch and continuous liquid-liquid separation. In addition, the disclosed embodiments are configured to identify a minimum number of velocity groups for the coupled computational fluid dynamics-population balance method (CFD-PBM) simulation of batch gravity separation modeling. Such modeling can be adapted to provide software systems for analyzing the design of proposed separator systems. Similarly, the exemplary modeling methods can be deployed in a control system for actively monitoring and controlling the operation of an existing separator system in real-time during operation for the purposes of active control to improve operation and efficiency. For example, in one or more embodiments, one or more operational input parameters of the separator can be adjusted before, during, and/or after the real-time operation of the separator based on the results of the CFD simulations in order to optimize the liquid-liquid separation efficiency of the separator. The adjustments of the input parameters allow the separator to separate and output one or more processed streams (e.g., water liquid stream, oil liquid stream) from the immiscible liquid dispersion, in which the amount of immiscible liquid dispersion (e.g., water-in-oil, oil-in-water, water-in-oil-in-water, or oil-in-water-in-oil emulsions) in the processed liquid streams is minimized.

Additionally, active level and pressure control in the separator adjusted based on proxy or reduced-order models based on the CFD simulations. Also, scenarios can be developed based on the CFD simulation for optimal positioning of the liquid/oil level and oil-water interface level through adjusting the control valves on the gas, oil, and water outlet streams. Further, dynamic adjustments of internal devices such as porous baffles or the inlet flow conditioner can be made based on CFD simulation data for different operating conditions.

In one or more embodiments, the CFD simulation data can be stored in a database that can be searched, interrogated and analyzed to automate selection of operating conditions (liquid and interface levels, demulsifier inject rates) based on current and forecast operating conditions of gas, oil, water flowrates, and temperature to reduce variability of separation efficiency (e.g., increase the interface level to increase retention time for oil-in-water separation, or adjust demulsifier chemical injection due to CFD simulation data showing increased thickness of emulsion band).

The subject matter described above is provided by way of illustration only and should not be construed as limiting. The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

While the present invention has been described above using several specific examples and embodiments, there are modifications and variations that will be apparent to those having ordinary skill in the art. As such, the described embodiments are to be considered in all respects as illustrative, and not restrictive. Therefore, the scope of the invention is indicated by the appended claims, rather than by the foregoing description. All changes that come within the meaning and range of equivalency of the claims are to be embraced within their scope.

What is claimed is:

1. A computer implemented method to evaluate the performance of a multiphase separator system for separating a multi-liquid and multi-phase immiscible liquid dispersion comprising the steps of:
providing operational input parameters at a hardware processor of a controller computing device, wherein the processor is configured by executing program code that is in the form of one or more software modules and stored in a non-transitory storage medium, and wherein the operational input parameters include:

fluid property data for the immiscible liquid dispersion including one or more of density, viscosity and surface tension, static or dynamic settling data for the immiscible liquid dispersion, and geometry of an internal volume of the separator including one or more internal geometric components therein;

generating, with the processor, a computational fluid dynamics (CFD) model of the separator system, wherein generating the CFD model includes:

defining, with the processor based on the geometry, a three-dimensional geometric model of the internal volume of the separator and the internal components therein, defining, with the processor based on the three-dimensional model, a computational mesh representing the internal volume of the separator, determining, with the processor, an initial droplet size distribution of the immiscible liquid dispersion contained within the internal volume, representing volumes for each of a continuous or dispersed gas phase, a continuous or dispersed heavier liquid phase and a continuous or dispersed lighter liquid phase within the interior volume of the separator using a Eulerian multiphase model, representing, for a volume of a dispersed liquid phase within the interior volume, a droplet size distribution using population balance modeling, wherein the distribution is modeled by solving a population balance equation according to multivariate methods, applying, with the processor, coalescence and breakage kernels to model droplet size evolution in the population as a function of droplet size and the fluid property data, and generating a model of a phase interaction between the dispersed liquid phase and the continuous liquid phase, wherein the model of the phase interaction is a function of a dispersed phase fraction concentration between a dilute regime, a semi-dilute regime and a concentrated regime of the dispersed liquid phase volume and is a function of a dispersed phase droplet diameter and the fluid property data; and outputting, with the processor based on the CFD model, one or more of the operational input parameters, wherein the output one or more operational parameters are adjusted based on the CFD model to maximize a separation efficiency of the separator;

controlling, with the processor, the separator according to the one or more operational input parameters, wherein the controlling step comprises sending, by the processor to the separator over a communication interface, a control signal configured to adjust a setting of one or more of a water stream outlet control valve, an oil stream outlet control valve, an operating temperature of the separator, a demulsifier chemical injection, an inlet control valve and a gas outlet control valve as a function of the one or more operational input parameters;

and outputting from the separator one or more streams of processed liquids separated from the immiscible liquid dispersion, wherein the one or more processed liquid streams are selected from the group consisting of a water liquid stream and an oil liquid stream;

monitoring, with the processor, a liquid-liquid separation efficiency of the separator in real-time during operation of the separator using one or more sensors exposed to respective outlet streams, wherein the liquid-liquid separator efficiency is determined by measuring one or more of a fraction of water in the oil outlet stream and a fraction of oil in the water outlet stream; and dynamically performing, with the processor during operation of the separator based on the monitoring step, the providing, generating, outputting and controlling steps such that the monitored liquid-liquid separation efficiency of the separator is maximized and the one or more streams of processed liquids separated from the immiscible liquid dispersion contain less than a prescribed amount of the immiscible liquid dispersion therein.

2. The process of claim 1, wherein the immiscible liquid dispersion comprises an emulsion selected from the group consisting of: an oil in water emulsion; a water in oil emulsion; water-in-oil-in-water emulsion; and oil-in-water-in-oil emulsion.

3. The process of claim 2, wherein the static or dynamic settling data is obtained using a bottle test or container testing or separator vessel testing, and wherein the step of providing the static or dynamic settling data includes monitoring the liquid dispersion in real-time during operation of the separator to determine a time-varying vertical distribution of a settling or rising phase in the separator.

4. The process of claim 3, wherein the time varying vertical distribution is determined by the processor using a sensor device provided within one or more of the internal volume of the separator, the inlet stream and the one or more outlet streams of the separator and configured to take one or more of: ultrasonic measurements, gamma densitometry measurements, nuclear magnetic resonance NMR measurements, and electrical tomography measurements of the liquid dispersion.

5. The process of claim 4, wherein the time-varying vertical distribution is measured in the separator and utilized by the processor to dynamically perform the steps of generating the CFD model, outputting the one or more of the operational input parameters, and controlling the separator.

6. The process of claim 3, further comprising: selecting, with the processor, the coalescence and breakage kernels based on the static or dynamic settling data.

7. The process of claim 1, wherein the control signal is configured to adjust the setting of one or more of the water stream outlet control valve, the oil stream outlet control valve and the inlet valve to define a liquid level and an interface level within the internal volume as a function of the one or more operational input parameters, and wherein the control signal adjusts the setting of the gas outlet control valve to achieve a pressure within the internal volume as a function of the one or more operational input parameters.

8. The process of claim 1, wherein the fluid property data comprises values or gradients of values for one or more variables including: density, viscosity, surface tension, momentum, velocity, turbulence energy dissipation rate, turbulent kinetic energy, and demulsifier or surfactant concentration.

9. The process of claim 8, wherein droplet size evolution is modeled as a function of droplet size and one or more of the fluid property data variables.

10. A method for optimizing liquid-liquid separation efficiency in a multiphase separator system comprising the steps of:

providing a multiphase separator having an inlet for receiving a multi-liquid and multiphase immiscible liquid dispersion comprising a gas phase, an oil phase, and a water phase; passing the immiscible liquid dispersion into the separator;

electronically providing operational input parameters from a connected electronic device to a hardware processor of a controller computing device, wherein the processor is configured by executing code that is in the form of one or more software modules and stored in a non-transitory storage medium, and wherein the operational input parameters include:

fluid property data for the immiscible liquid dispersion including one or more of density, viscosity and surface tension, static or dynamic settling data for the immiscible liquid dispersion, and geometry of an internal volume of the separator including one or more internal geometric components therein;

generating, with the processor, a computational fluid dynamics (CFD) model of the separator system, wherein generating the CFD model includes:

defining, with the processor executing code comprising a CFD model generator module, based on the geometry, a three-dimensional geometric model of the internal volume of the separator and the internal components therein, defining, with the processor executing code comprising the CFD model generator module, based on the three-dimensional model, a computational mesh representing the internal volume of the separator, determining, with the processor with the processor executing code comprising an input parameters module and the CFD model generator module, an initial droplet size distribution of the immiscible liquid dispersion contained within the internal volume, representing, with the processor with the processor executing code comprising the input parameters module and the CFD model generator module, volumes for each of a continuous or dispersed gas phase, a continuous or dispersed heavier liquid phase and a continuous or dispersed lighter liquid phase within the interior volume of the separator using a Eulerian multiphase model, representing, with the processor executing code comprising the input parameters module and the CFD model generator module, for a volume of a dispersed liquid phase within the interior volume, a droplet size distribution using population balance modeling, wherein the distribution is modeled by solving a population balance equation according to multivariate methods, applying, with the processor executing code comprising the input parameters module and the CFD model generator module, coalescence and breakage kernels to model droplet size evolution in the population as a function of droplet size and the fluid property data, and generating, with the processor executing code comprising a simulation module and the CFD model generator module, a model of a phase interaction between the continuous liquid phase and the dispersed liquid phase, wherein the model of the phase interaction is a function of a dispersed phase fraction concentration between a dilute regime, a semi-dilute regime and a concentrated regime of the dispersed liquid phase volume and is a function of a dispersed phase droplet diameter and the liquid phase properties;

adjusting, with the processor executing code comprising an adjustment module and the CFD model generator module, based on the CFD model, one or more of the operational input parameters to maximize the liquid-liquid separation efficiency;

controlling, with the processor, the separator according to the one or more operational input parameters, wherein the controlling step comprises sending, by the processor to the separator over a communication interface, a control signal configured to adjust a setting of one or more of a water stream outlet control valve, an oil stream outlet control valve, an operating temperature of the separator, a demulsifier chemical injection, an inlet control valve and a gas outlet control valve as a function of the one or more operational input parameters;

outputting from the separator one or more streams of processed liquids separated from the immiscible liquid dispersion and containing minimal amounts of the immiscible liquid dispersion, wherein the one or more processed liquid streams are selected from the group consisting of a water outlet stream and an oil outlet stream;

monitoring a liquid-liquid separation efficiency of the separator in real-time during operation of the separator using one or more sensors exposed to respective outlet streams, wherein the liquid-liquid separator efficiency is determined by measuring one or more of a fraction of water in the oil outlet stream and a fraction of oil in the water outlet stream; and dynamically performing, by the processor based on the monitoring step, the steps for providing operational input parameters, generating the CFD model, adjusting the operational input parameters, controlling the separator, outputting and monitoring the one or more liquid streams, such that the separation efficiency is maximized and the one or more streams of processed liquids separated from the immiscible liquid dispersion contain less than a prescribed amount of the immiscible liquid dispersion therein.

11. The process of claim 10, wherein the immiscible liquid dispersion comprises an emulsion selected from the group consisting of: an oil in water emulsion; a water in oil emulsion; water-in-oil-in-water emulsion; and oil-in-water-in-oil emulsion.

12. The process of claim 10, wherein the control signal is configured to adjust the setting of one or more of the water stream outlet control valve, the oil stream outlet control valve and the inlet valve to define a liquid level and an interface level within the internal volume as a function of the one or more operational input parameters, and wherein the control signal adjusts the setting of the gas outlet control valve to achieve a pressure within the internal volume as a function of the one or more operational input parameters.

13. The process of claim 12, wherein the static or dynamic settling data is obtained using a bottle test or container testing or separator vessel testing, and wherein the step of providing the static or dynamic settling data includes monitoring the immiscible liquid dispersion in real-time during operation of the separator to determine a time-varying vertical distribution of a settling or rising phase in the separator.

14. The process of claim 13, further comprising: selecting, with the processor, the coalescence and breakage kernels based on the static or dynamic settling data.

15. The process of claim 13, wherein the time varying vertical distribution is determined by the processor using a sensor device provided within one or more of the internal volume of the separator, the inlet stream and the one or more outlet streams of the separator and configured to take one or more of: ultrasonic measurements, gamma densitometry measurements, nuclear magnetic resonance NMR measurements, and electrical tomography measurements of the liquid dispersion.

16. The process of claim 15, wherein the time-varying vertical distribution is measured in the separator and is utilized by the processor to dynamically perform the steps of generating the CFD model, outputting the one or more of the operational input parameters, and controlling the separator.

17. The process of claim 1, wherein the fluid property data comprises values or gradients of values for one or more variables including: density, viscosity, surface tension, momentum, velocity, turbulence energy dissipation rate, turbulent kinetic energy, and demulsifier or surfactant concentration.

18. The process of claim 17, wherein droplet size evolution is modeled as a function of droplet size and one or more of the fluid property data variables.

19. The process of claim 10, wherein the initial droplet size distribution is determined from experimental measurements and includes the initial droplet diameter distribution and phase fractions for each probability distribution function defined by the probability distribution of droplets in terms of the volume fraction divided by the droplet diameter.

20. The process of claim 10, wherein the internal geometric components include one or more of: inlet devices, perforated plates, baffles, vortex breakers, weirs, coalescer packs, and devices obstructing or partially obstructing the flow of gas and liquid within the internal volume of the separator.

* * * * *